US011351317B2

(12) United States Patent
Calderon Oliveras et al.

(10) Patent No.: US 11,351,317 B2
(45) Date of Patent: Jun. 7, 2022

(54) DRUG DELIVERY DEVICE WITH ELECTRONICS

(71) Applicant: Norton (Waterford) Limited, Waterford (IE)

(72) Inventors: Enrique Calderon Oliveras, Waterford (IE); Carl L. Lewis, Cambridgeshire (GB); Symon D'Oyly Cotton, Cambridge (GB); Steven D. Gardner, Peterborough (GB); Robert O. Kivlin, Cambridge (GB)

(73) Assignee: Norton (Waterford) Limited, Waterford (IE)

( * ) Notice: Subject to any disclaimer, the term of this patent is extended or adjusted under 35 U.S.C. 154(b) by 85 days.

(21) Appl. No.: 16/148,046

(22) Filed: Oct. 1, 2018

(65) Prior Publication Data
US 2019/0030263 A1   Jan. 31, 2019

Related U.S. Application Data

(63) Continuation of application No. 15/815,758, filed on Nov. 17, 2017.
(Continued)

(51) Int. Cl.
*A61M 15/00* (2006.01)
*G16H 20/13* (2018.01)
(Continued)

(52) U.S. Cl.
CPC ...... *A61M 15/008* (2014.02); *A61M 15/0001* (2014.02); *A61M 15/009* (2013.01);
(Continued)

(58) Field of Classification Search
CPC ............ A61M 15/008; A61M 15/0065; A61M 15/0091; A61M 15/0026; A61M 15/0071;
(Continued)

(56) References Cited

U.S. PATENT DOCUMENTS

| 4,495,944 A | 1/1985 | Brisson et al. |
| 4,984,158 A | 1/1991 | Hillsman |

(Continued)

FOREIGN PATENT DOCUMENTS

| EP | 0667168 A1 | 8/1995 |
| EP | 0933092 A1 | 8/1999 |

(Continued)

OTHER PUBLICATIONS

JP 2016515410 A, U.S. 2014/0261443 A1.

*Primary Examiner* — Tu A Vo
(74) *Attorney, Agent, or Firm* — Flaster Greenberg, P.C.

(57) ABSTRACT

A device for delivering medication to a user may include a main body, an electronics module, and a slider. The main body may include a mouthpiece, a medication reservoir, and a mouthpiece cover, where the mouthpiece cover may be hinged to the main body. The electronics module may include a communication circuit, a pressure sensor, and a switch. The slider may be configured to engage the switch when the mouthpiece cover moves from a closed position to an open position. The switch may be configured to switch the electronics module from an off state or a sleep state to an active state. The electronics module may be configured to never return to the off state after the mouthpiece cover is moved to expose the mouthpiece for the first time by the user.

20 Claims, 12 Drawing Sheets

Related U.S. Application Data

(60) Provisional application No. 62/424,306, filed on Nov. 18, 2016.

(51) Int. Cl.
   *G16H 20/17* (2018.01)
   *A61M 16/00* (2006.01)

(52) U.S. Cl.
   CPC .... *A61M 15/0026* (2014.02); *A61M 15/0065* (2013.01); *A61M 15/0071* (2014.02); *A61M 15/0083* (2014.02); *A61M 15/0091* (2013.01); *A61M 15/0095* (2014.02); *A61M 15/0096* (2014.02); *G16H 20/13* (2018.01); *G16H 20/17* (2018.01); *A61M 15/00* (2013.01); *A61M 15/0005* (2014.02); *A61M 2016/0018* (2013.01); *A61M 2016/0027* (2013.01); *A61M 2205/3306* (2013.01); *A61M 2205/3331* (2013.01); *A61M 2205/3334* (2013.01); *A61M 2205/3368* (2013.01); *A61M 2205/3553* (2013.01); *A61M 2205/3569* (2013.01); *A61M 2205/3576* (2013.01); *A61M 2205/3584* (2013.01); *A61M 2205/3592* (2013.01); *A61M 2205/50* (2013.01); *A61M 2205/505* (2013.01); *A61M 2205/52* (2013.01); *A61M 2205/581* (2013.01); *A61M 2205/583* (2013.01); *A61M 2205/584* (2013.01); *A61M 2205/587* (2013.01); *A61M 2205/8206* (2013.01)

(58) Field of Classification Search
   CPC ............ A61M 15/0083; A61M 15/009; A61M 2205/3334; A61M 15/00; A61M 2205/3331; A61M 2205/3576; A61M 2205/3584; A61M 2205/50; A61M 2205/52; A61M 2205/8206; A61M 15/0093–0096; G16H 20/17
   See application file for complete search history.

(56) References Cited

U.S. PATENT DOCUMENTS

| | | | |
|---|---|---|---|
| 5,333,106 A | 7/1994 | Lanpher et al. | |
| 5,363,842 A | 11/1994 | Mishelevich et al. | |
| 5,809,997 A | 9/1998 | Wolf | |
| 5,839,429 A | 11/1998 | Marnfeldt et al. | |
| 5,842,468 A | 12/1998 | Denyet et al. | |
| 5,887,586 A | 3/1999 | Dahlback et al. | |
| 6,138,669 A | 10/2000 | Rocci, Jr. et al. | |
| 6,285,731 B1 | 9/2001 | Marnfeldt et al. | |
| 6,390,088 B1 | 5/2002 | Nohl et al. | |
| 6,958,691 B1 | 10/2005 | Anderson et al. | |
| 6,978,780 B1 | 12/2005 | Marnfeldt et al. | |
| 6,990,975 B1 | 1/2006 | Jones et al. | |
| 7,072,738 B2 | 7/2006 | Bonney et al. | |
| 7,151,456 B2 | 12/2006 | Godfrey et al. | |
| 7,191,777 B2 | 3/2007 | Brand et al. | |
| 7,198,172 B2 | 4/2007 | Harvey et al. | |
| 7,233,228 B2 | 6/2007 | Lintell et al. | |
| 7,249,687 B2 | 7/2007 | Anderson et al. | |
| 7,347,200 B2 | 3/2008 | Jones et al. | |
| 7,383,837 B2 | 6/2008 | Robertson et al. | |
| 7,424,888 B2 | 9/2008 | Harvey et al. | |
| 7,495,546 B2 | 2/2009 | Lintell et al. | |
| 7,837,648 B2 | 11/2010 | Blair et al. | |
| 8,231,573 B2 | 7/2012 | Edwards et al. | |
| 8,240,301 B2 | 8/2012 | Spaargaren et al. | |
| 8,424,517 B2 | 4/2013 | Sutherland et al. | |
| 8,464,707 B2 | 6/2013 | Jongejan et al. | |
| 8,547,239 B2 | 10/2013 | Peatfield et al. | |
| 8,746,238 B2 | 6/2014 | Kohnle | |
| 8,807,131 B1 | 8/2014 | Tunnell et al. | |
| 8,960,189 B2 | 2/2015 | Morrison et al. | |
| 8,997,735 B2 | 4/2015 | Zierenberg et al. | |
| 9,056,174 B2 | 6/2015 | Bradshaw et al. | |
| 9,174,009 B2 | 11/2015 | Peatfield et al. | |
| 9,188,579 B2 | 11/2015 | Shen et al. | |
| 9,242,056 B2 | 1/2016 | Andersen et al. | |
| 9,339,616 B2 | 5/2016 | Denny et al. | |
| 9,364,619 B2 | 6/2016 | Overfield et al. | |
| 9,427,534 B2 | 8/2016 | Bruin et al. | |
| 9,463,291 B2 | 10/2016 | Imran et al. | |
| 9,468,729 B2 | 10/2016 | Sutherland et al. | |
| 9,550,031 B2 | 1/2017 | Van Sickle et al. | |
| 9,555,200 B2 | 1/2017 | Hosemann et al. | |
| 9,555,201 B2 | 1/2017 | Collins et al. | |
| 9,694,147 B2 | 7/2017 | Peatfield et al. | |
| 9,736,642 B2 | 8/2017 | Ostrander et al. | |
| 9,839,398 B2 | 12/2017 | Yamamori et al. | |
| 9,872,964 B2 | 1/2018 | Cline et al. | |
| 9,911,308 B2 | 3/2018 | Edwards et al. | |
| 9,943,656 B2 | 4/2018 | Shears et al. | |
| 9,956,360 B2 | 5/2018 | Germinario et al. | |
| 9,962,507 B2 | 5/2018 | Germinario et al. | |
| 9,962,508 B2 | 5/2018 | Bruin et al. | |
| 10,016,134 B2 | 7/2018 | Hansen et al. | |
| 10,046,121 B2 | 8/2018 | Kolb et al. | |
| 10,406,305 B2 | 9/2019 | Collins et al. | |
| 2002/0000225 A1 | 1/2002 | Schuler et al. | |
| 2002/0078949 A1 | 6/2002 | Oleary | |
| 2002/0079326 A1* | 6/2002 | Fuchs | B05B 11/308 222/38 |
| 2002/0124852 A1 | 9/2002 | Gonda et al. | |
| 2002/0148469 A1 | 10/2002 | OLeary et al. | |
| 2002/0185128 A1 | 12/2002 | Theobald et al. | |
| 2003/0183226 A1* | 10/2003 | Brand | A61M 16/161 128/200.23 |
| 2003/0192535 A1 | 10/2003 | Christrup et al. | |
| 2003/0205229 A1 | 11/2003 | Crockford et al. | |
| 2004/0069301 A1* | 4/2004 | Bacon | G01H 1/12 128/200.23 |
| 2004/0089299 A1 | 5/2004 | Bonney et al. | |
| 2004/0117062 A1 | 6/2004 | Bonney et al. | |
| 2004/0187869 A1* | 9/2004 | Bjorndal | G09B 23/28 128/203.15 |
| 2005/0119604 A1 | 6/2005 | Bonney et al. | |
| 2005/0161467 A1 | 7/2005 | Jones et al. | |
| 2005/0247305 A1* | 11/2005 | Zierenberg | A61M 15/008 128/200.14 |
| 2005/0247312 A1 | 11/2005 | Davies et al. | |
| 2005/0251289 A1 | 11/2005 | Bonney et al. | |
| 2006/0243275 A1* | 11/2006 | Ruckdeschel | A61M 11/001 128/200.23 |
| 2007/0021715 A1 | 1/2007 | Kohlbrenner et al. | |
| 2007/0056580 A1 | 3/2007 | Jones et al. | |
| 2007/0235026 A1 | 10/2007 | Hamano | |
| 2008/0173301 A1 | 7/2008 | Deaton et al. | |
| 2008/0178872 A1* | 7/2008 | Genova | A61M 15/0026 128/200.23 |
| 2008/0230057 A1 | 9/2008 | Sutherland et al. | |
| 2008/0314383 A1 | 12/2008 | Barney et al. | |
| 2009/0020113 A1* | 1/2009 | Watanabe | A61M 15/025 128/200.14 |
| 2009/0221308 A1 | 9/2009 | Lerner et al. | |
| 2010/0180890 A1* | 7/2010 | Nobutani | A61M 15/025 128/203.12 |
| 2010/0242960 A1 | 9/2010 | Zangerle et al. | |
| 2010/0250280 A1 | 9/2010 | Sutherland et al. | |
| 2010/0252036 A1 | 10/2010 | Sutherland et al. | |
| 2010/0282255 A1 | 11/2010 | Hamano | |
| 2011/0169456 A1 | 7/2011 | Wang et al. | |
| 2011/0253139 A1 | 10/2011 | Guthrie et al. | |
| 2011/0282693 A1 | 11/2011 | Craft et al. | |
| 2012/0048269 A1 | 3/2012 | Pardonge et al. | |
| 2012/0048270 A1 | 3/2012 | Pardonge | |
| 2013/0008436 A1 | 1/2013 | Von Hollen et al. | |
| 2013/0269685 A1 | 10/2013 | Wachtel et al. | |
| 2013/0269694 A1* | 10/2013 | Patton | A61M 15/008 128/203.14 |
| 2013/0276799 A1* | 10/2013 | Davidson | A61M 15/0065 131/273 |

(56) References Cited

U.S. PATENT DOCUMENTS

| | | |
|---|---|---|
| 2013/0298905 A1 | 11/2013 | Levin et al. |
| 2014/0007867 A1 | 1/2014 | Bruin et al. |
| 2014/0053833 A1* | 2/2014 | Cline ................ A61M 15/008 128/203.12 |
| 2014/0106324 A1 | 4/2014 | Adams et al. |
| 2014/0116426 A1 | 5/2014 | Mullinger et al. |
| 2014/0182584 A1 | 7/2014 | Sutherland et al. |
| 2014/0261443 A1 | 9/2014 | Lowenstein et al. |
| 2015/0099726 A1 | 4/2015 | Dalvi et al. |
| 2015/0273165 A1* | 10/2015 | Hadash ............... A61M 15/002 128/203.14 |
| 2015/0283341 A1 | 10/2015 | Adams et al. |
| 2015/0332379 A1* | 11/2015 | Alarcon ............. G06F 16/9554 705/26.81 |
| 2016/0001018 A1 | 1/2016 | Fink et al. |
| 2016/0051776 A1* | 2/2016 | Von Hollen ........ A61M 15/008 128/200.23 |
| 2016/0082208 A1 | 3/2016 | Ballam et al. |
| 2016/0128389 A1 | 5/2016 | Lamb et al. |
| 2016/0129182 A1 | 5/2016 | Schuster et al. |
| 2016/0144141 A1* | 5/2016 | Biswas ................ G16H 20/10 128/200.23 |
| 2016/0166766 A1 | 6/2016 | Schuster et al. |
| 2016/0206559 A1 | 7/2016 | Dalvi et al. |
| 2016/0228657 A1 | 8/2016 | Sutherland et al. |
| 2016/0256639 A1 | 9/2016 | Van Sickle et al. |
| 2016/0303336 A1 | 10/2016 | Arp et al. |
| 2016/0303337 A1* | 10/2016 | Van Achthoven .......................... A61M 15/0086 |
| 2016/0314256 A1 | 10/2016 | Su et al. |
| 2016/0325057 A1 | 11/2016 | Morrison et al. |
| 2016/0325058 A1* | 11/2016 | Samson ................ A61B 5/087 |
| 2016/0339190 A1 | 11/2016 | Morrison et al. |
| 2016/0354562 A1* | 12/2016 | Morrison ............. G16H 40/63 |
| 2017/0079557 A1 | 3/2017 | Lauk et al. |
| 2017/0109493 A1 | 4/2017 | Hogg et al. |
| 2017/0132391 A1 | 5/2017 | Morrison |
| 2017/0140125 A1 | 5/2017 | Hogg et al. |
| 2017/0164892 A1 | 6/2017 | Sezan et al. |
| 2017/0173279 A1 | 6/2017 | Sutherland et al. |
| 2017/0246406 A1 | 8/2017 | Sutherland et al. |
| 2017/0258993 A1 | 9/2017 | Pizzochero et al. |
| 2017/0262613 A1 | 9/2017 | Ljungberg |
| 2017/0325734 A1 | 11/2017 | Sutherland et al. |
| 2017/0363673 A1 | 12/2017 | Mukherjee et al. |
| 2018/0011988 A1 | 1/2018 | Ziegler et al. |
| 2018/0043114 A1 | 2/2018 | Bowen et al. |
| 2018/0052964 A1 | 2/2018 | Adelson et al. |
| 2018/0056018 A1* | 3/2018 | Canvin ................ G16H 10/20 |
| 2018/0085540 A1 | 3/2018 | Dantsker et al. |
| 2018/0093053 A1 | 4/2018 | Turner et al. |
| 2018/0125365 A1 | 5/2018 | Hunter et al. |
| 2018/0161530 A1 | 6/2018 | Ganton et al. |
| 2018/0221600 A1 | 8/2018 | Shears et al. |
| 2019/0015608 A1 | 1/2019 | Glusher et al. |
| 2019/0030262 A1 | 1/2019 | Ziegler et al. |
| 2019/0105450 A1* | 4/2019 | Sutherland ........ A61M 15/0026 |
| 2019/0175847 A1 | 6/2019 | Pocreva, III et al. |
| 2020/0086069 A1* | 3/2020 | Riebe ................. A61M 15/009 |
| 2021/0008304 A1* | 1/2021 | Marcoz ............... A61M 15/008 |

FOREIGN PATENT DOCUMENTS

| | | |
|---|---|---|
| EP | 1135056 B1 | 8/2006 |
| EP | 1992381 A1 | 11/2008 |
| EP | 3228345 A1 | 10/2017 |
| EP | 3485930 A1 | 5/2019 |
| JP | H07509378 A | 10/1995 |
| JP | 2006187629 A | 7/2006 |
| JP | 2006212088 A | 8/2006 |
| JP | 2007289716 A | 11/2007 |
| JP | 2016515410 A | 5/2016 |
| JP | 2006187629 A | 2/2022 |
| WO | WO/1995/022365 A1 | 8/1995 |
| WO | 9964095 A2 | 12/1999 |
| WO | WO/1999/063901 A1 | 12/1999 |
| WO | WO 1999/064095 A2 | 12/1999 |
| WO | WO/2003/063754 A1 | 8/2003 |
| WO | 2006062941 A1 | 8/2006 |
| WO | WO 2008/070516 A2 | 6/2008 |
| WO | WO/2009/003989 A1 | 1/2009 |
| WO | WO 2011/157561 A1 | 12/2011 |
| WO | WO 2014/033229 A2 | 3/2014 |
| WO | WO 2015/031472 A1 | 3/2015 |
| WO | WO 2016/030521 A1 | 8/2015 |
| WO | WO 2016/033419 A1 | 8/2015 |
| WO | 2015/144442 A1 | 10/2015 |
| WO | WO/2016/043601 A1 | 3/2016 |
| WO | WO 2016111633 A1 | 7/2016 |
| WO | WO/2017/005605 A1 | 1/2017 |
| WO | WO/2017/051389 A1 | 3/2017 |
| WO | WO-2017051389 A1 * | 3/2017 ........... A61B 5/4833 |
| WO | WO/2017/129521 A1 | 8/2017 |
| WO | WO/2017/141194 A1 | 8/2017 |
| WO | WO/2017/176693 A1 | 10/2017 |
| WO | WO/2017/176704 A1 | 10/2017 |
| WO | WO 2017/178865 A1 | 10/2017 |
| WO | WO/2017/180980 A1 | 10/2017 |
| WO | WO/2017/189712 A1 | 11/2017 |
| WO | WO 2018091678 A1 | 5/2018 |
| WO | WO/2018/128976 A1 | 7/2018 |
| WO | WO2018/134552 A1 | 7/2018 |
| WO | WO/2018/134553 A1 | 7/2018 |
| WO | WO 2018149619 A1 | 8/2019 |

* cited by examiner

DRUG DELIVERY DEVICE WITH ELECTRONICS

CROSS-REFERENCE TO RELATED APPLICATIONS

This application is a continuation of U.S. patent application Ser. No. 15/815,758, filed Nov. 17, 2017, which claims the benefit of Provisional U.S. Patent Application No. 62/424,306, filed Nov. 18, 2016, the disclosure of which is incorporated herein by reference in its entirety.

BACKGROUND

Drug delivery devices facilitate the delivery of medication into a patient's body via various routes of administration. Typical routes of administration include oral, topical, sublingual inhalation, injection and the like. The devices may be used to deliver medications for the treatment various diseases, ailments and medical conditions. Inhalation devices, for example, may be used to treat asthma, chronic obstructive pulmonary disease (COPD) and cystic fibrosis (CF). While drug delivery devices are designed to deliver an appropriate dose of medication to a patient as part of a therapeutic treatment, the effectiveness of a particular treatment may be influenced by non-physiological factors, such as the patient's adherence and compliance.

In the context of a drug therapy, adherence may refer to the degree to which a patient is following a prescribed dosing regimen. For example, if the patient's prescription calls for two doses each day, and the patient is taking two doses per day, the patient may be considered 100% adherent. If the patient is only taking one dose per day, he or she may be deemed only 50% adherent. In the latter case, the patient may not be receiving the treatment prescribed by his or her doctor, which may negatively affect the efficacy of the therapeutic treatment.

Compliance may refer to a patient's technique when using a particular drug delivery device. If the patient is using the device in a manner that is recommended by a doctor or by a manufacturer, the device is likely to deliver the desired dose of medication and the patient may be deemed compliant. However, if the device is not being used properly during drug administration, the device's ability to deliver a proper dose of medication may be compromised. As such, the patient may be deemed non-compliant. In the case of an inhalation device, for example, the patient may need to achieve a minimum inspiratory effort to ensure a full dose of medication is delivered from the device into the patient's lungs. For some patients, such as children and the elderly, meeting the requirements for full compliance may be difficult due to physical limitations, such as limited lung function. Accordingly, like adherence, failing to achieve full compliance may reduce the effectiveness of a prescribed treatment.

A patient's ability to achieve full compliance may be further complicated by certain physical properties of the medication. For example, some respiratory medications may consist of fine particles and/or may lack any odor or taste. Thus, a patient using an inhalation device may not be able to correct a non-compliant use because he or she may not be able to immediately detect or sense that medication is being inhaled and/or know whether the amount of inhaled medication complies with the prescription.

SUMMARY

A drug delivery device may be adapted to include an electronics module that is configured to sense, track, and/or process usage conditions and parameters associated with the device (e.g., to improve adherence and compliance). The electronics module may be further configured to communicate the conditions and parameters to external devices, such as a smartphone, for similar and/or further processing. The inclusion of an electronics module in a drug delivery device opens the doors to a wealth of digital improvements and features to enhance the use of the device. The electronics module, in this context, may create a platform to leverage helpful smartphone applications and powerful data analytics. However, the introduction of electronics into any drug delivery device may introduce certain technical challenges, such as durability, reliability, electro-mechanical integration, power management, and drug delivery performance. The present disclosure provides solutions for inclusion of certain electrical components with a drug delivery device, such as an inhaler.

Examples of inhalation devices (e.g., breath-actuated inhalers) are provided herein. The inhalation device may include a main body having a mouthpiece and a mouthpiece cover, a slider at least partially disposed within the main body, and an electronics module having a switch and a pressure sensor. The electronics module may be configured to be in an off state prior to a user moving the mouthpiece cover to expose the mouthpiece for the first time. When the mouthpiece cover is moved to expose the mouthpiece, the slider may be configured to engage the switch, which may cause the electronics module to transition from the off state to an active state and to sense inhalation by the user through the mouthpiece. The electronics module may be configured to not return to the off state after the mouthpiece cover is moved to expose the mouthpiece for the first time by the user (e.g., throughout the life of the inhalation device and/or battery). The electronics module may be configured to start an internal counter when transitioning from the off state. The electronics module is configured to timestamp inhalation events, inhalation metrics, error events, pressure measurements, mouthpiece cover opening events, etc. based on the internal counter.

The pressure sensor may be configured to measure a plurality of pressure changes within the inhaler resulting from the user's inhalation through the mouthpiece after the mouthpiece cover is moved from the closed position to the open position. The pressure sensor may be configured to take measurements for a predetermined period of time or until a predetermined event is detected (e.g., an inhalation, a closing of the mouthpiece cover, etc.). The electronics module may also include a processor configured to determine one or more inhalation parameters based on the plurality of measured pressure changes. The inhalation parameters may include, but are not limited to, a peak flow rate, a time to peak flow rate, an inhaled volume, and an inhalation duration. The electronics module may also include a communications circuit configured to wirelessly transmit the inhalation parameters to an external device.

When in the active state, the electronics module may be configured to measure one or more pressure changes within the inhaler resulting from the user's inhalation through the mouthpiece, determine inhalation parameters based on the one more measured pressure changes, store the inhalation parameters in a local memory, advertise to an external device, and/or transmit the inhalation parameters to the external device.

The electronics module may be configured to be in a sleep state when not in the off state or the active state. The electronics module may be configured to change from the active state to the sleep state upon the electronics module determining that the pressure measurement received from a pressure sensor does not fall within the predetermined range for a predetermined amount of time (e.g., a user not inhaling from the mouthpiece for the predetermined amount of time), where the predetermined amount of time is based on the internal counter. The electronics module may be configured to store a timeout event and associated timestamp when the mouthpiece cover is moved to the open position and the electronics module does not determine that a pressure measurement received from the pressure sensor is within the predetermined range within the predetermined amount of time (e.g., a user not inhaling from the mouthpiece for the predetermined amount of time), where the timestamp of the timeout event is based on the internal counter.

Upon determining that the pressure measurement received from a pressure sensor is within the predetermined range, the electronics module may be configured to generate an inhalation event and associated timestamp for the inhalation event, and store the inhalation event and associated timestamp in memory of the inhaler, where the timestamp of the inhalation event based on the internal counter. Upon storing the inhalation event and associated timestamp in memory, the electronics module may be configured to cause the communication circuit to transmit advertisements at a first advertising rate in an attempt to sync up with an external device. If the communication circuit successfully syncs with the external device, the communication circuit may be configured to transmit the inhalation event and associated timestamp to the external device. If the communication circuit does not successfully sync with the external device after a predetermined amount of time, the communication circuit may be configured to transmit the advertisements at a second advertising rate that is slower than the first advertising rate.

The electronics module may be configured to transition between the active state and a sleep state at the first rate when the mouthpiece cover is in the closed position. The electronics module may be configured to cause the communication circuit to transmit advertisements at a first advertising rate in an attempt to sync up with an external device when the mouthpiece cover is in the open position, and transmit advertisements at a second advertising rate that is slower than the first advertising rate when the mouthpiece cover is in the closed position.

When in the active state, the electronics module may be configured to sample pressure measurements received from a pressure sensor at a predetermined rate, and configured to power off the sensor system between the sampling times of the pressure measurements received from the pressure sensor. The electronics module may be configured to perform calculations on the pressure measurements received from the pressure sensor between the sampling times. The electronics module may be configured to change from the active state to a sleep state upon the mouthpiece cover returning to the closed position.

A system comprising: a mobile application; and a breath-actuated inhaler for delivering medication to a user, the inhaler comprising a mouthpiece, a mouthpiece cover, an electronics module, and a medication reservoir, the mouthpiece cover hinged to the main body, and the electronics module comprising a communication circuit, a power supply, a sensor system, a battery, and a switch; wherein the electronics module is configured to start an internal counter when the mouthpiece cover is first moved from a closed position to an open position by a user; wherein the mobile application is configured to query the breath-actuated inhaler to retrieve event data, the event data comprising a mouthpiece cover opening event, a timestamp, and inhalation profile information.

The electronics module is configured to run the internal counter upon when the mouthpiece cover is in the closed position and in the open position after the first time the mouthpiece cover is moved to the open position by the user. The inhalation profile information comprises one or more of peak flow of pressure data provided by the sensor system, volume of the pressure data, time-to-peak of the pressure data, or duration of the pressure data. The event data comprises one or more of a status flag indicating whether an inhalation event was low inhalation, good inhalation, no inhalation, or an exhalation. The event data comprises information relating to whether the mouthpiece cover is in the open position or the closed position.

DETAILED DESCRIPTION

The present disclosure describes devices, systems and methods for sensing, tracking and/or processing usage conditions and parameters associated with a drug delivery device. The devices, systems and methods are described in the context of a breath-actuated inhalation device for delivering medication into a user's lungs. However, the described solutions are equally applicable to other drug delivery devices, such as an injector, a metered-dose inhaler, a nebulizer, a transdermal patch, or an implantable.

Figure 1:
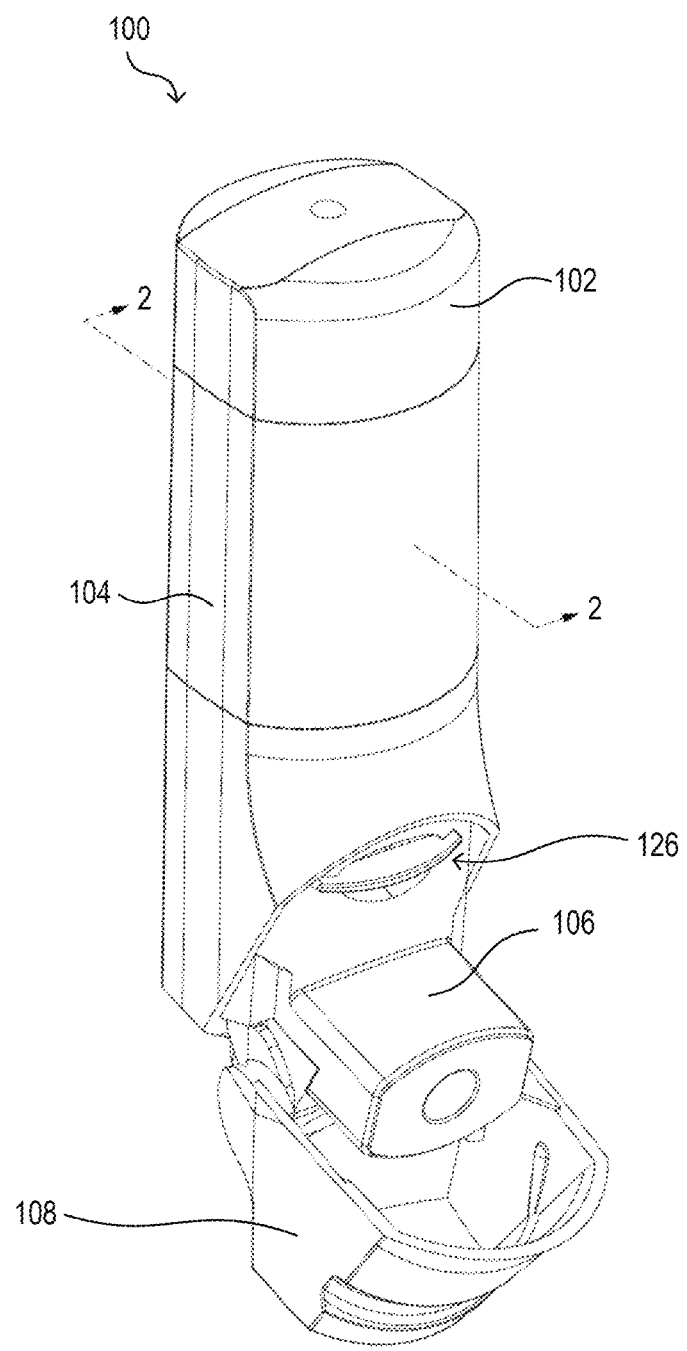
FIG. 1 is a front perspective view of an example inhalation device.
Figure 2:
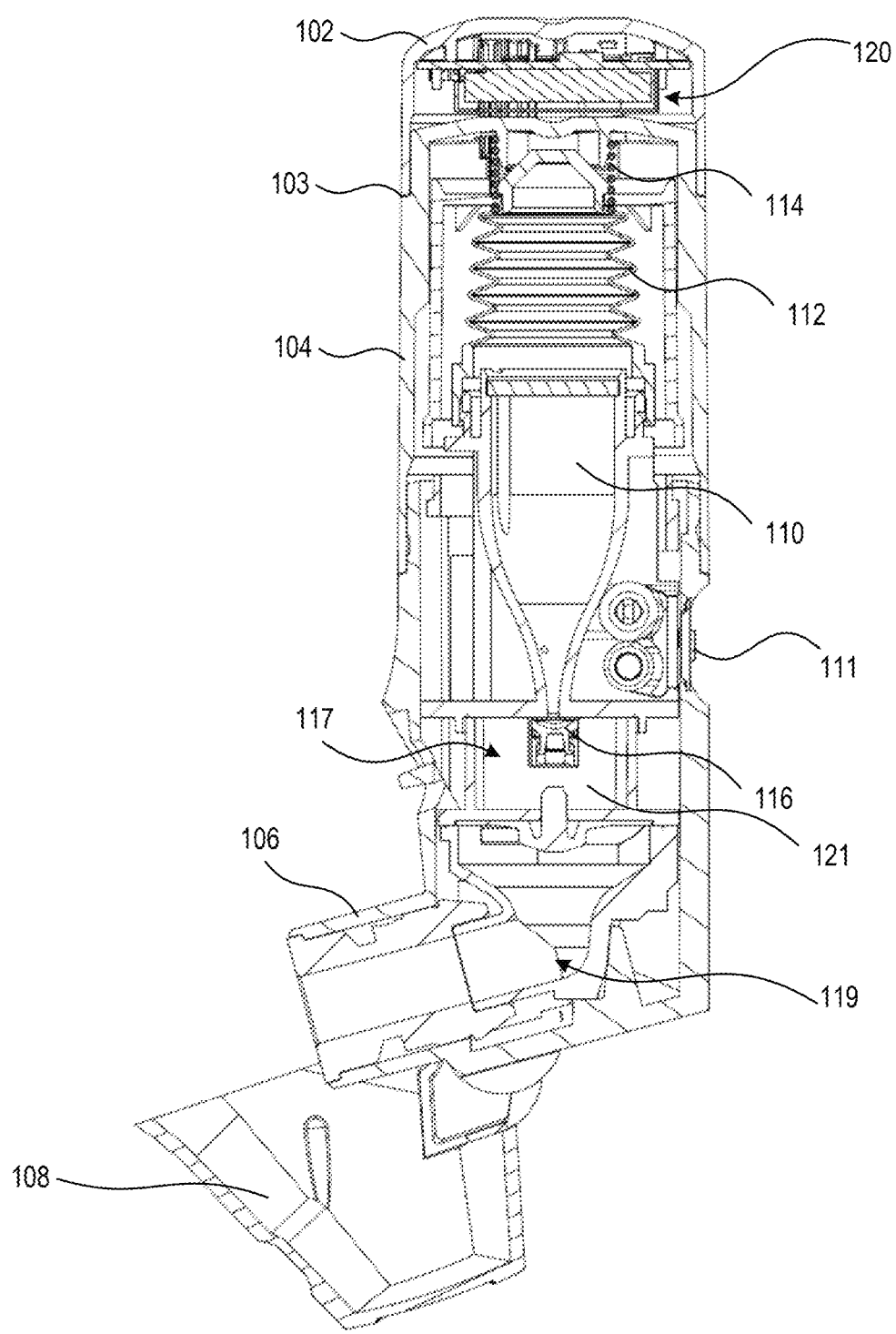
FIG. 2 is a cross-sectional interior perspective view of the example inhalation device of FIG. 1.
Figure 3:
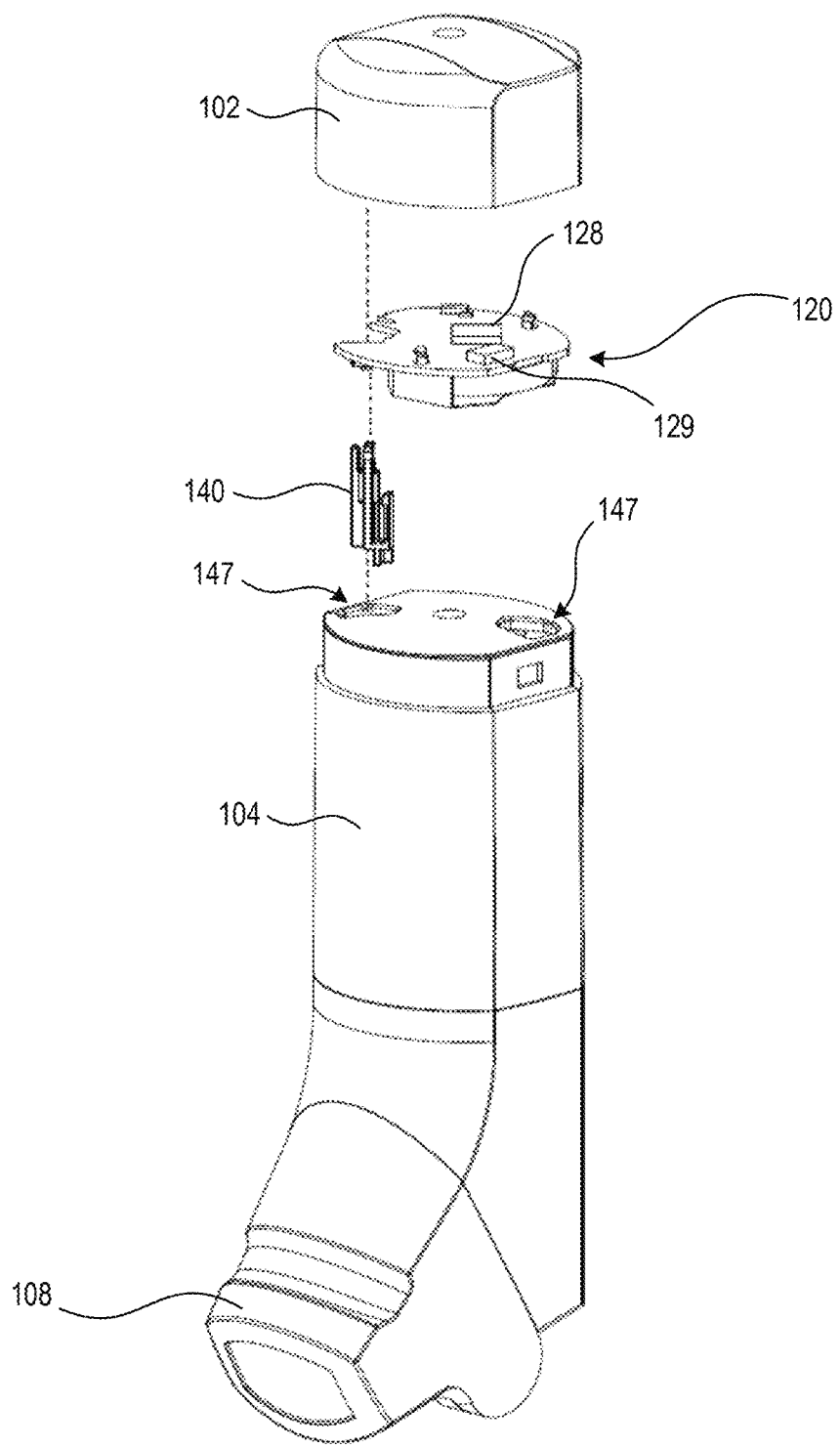
FIG. 3 is an exploded perspective view of the example inhalation device of FIG. 1 with a top cap removed to expose an electronics module.

FIG. 1 is a front perspective view of an example inhalation device 100. FIG. 2 is a cross-sectional interior perspective view of the example inhalation device 100. FIG. 3 is an exploded perspective view of the example inhalation device 100 with a top cap removed to expose an electronics module.

Figure 4:
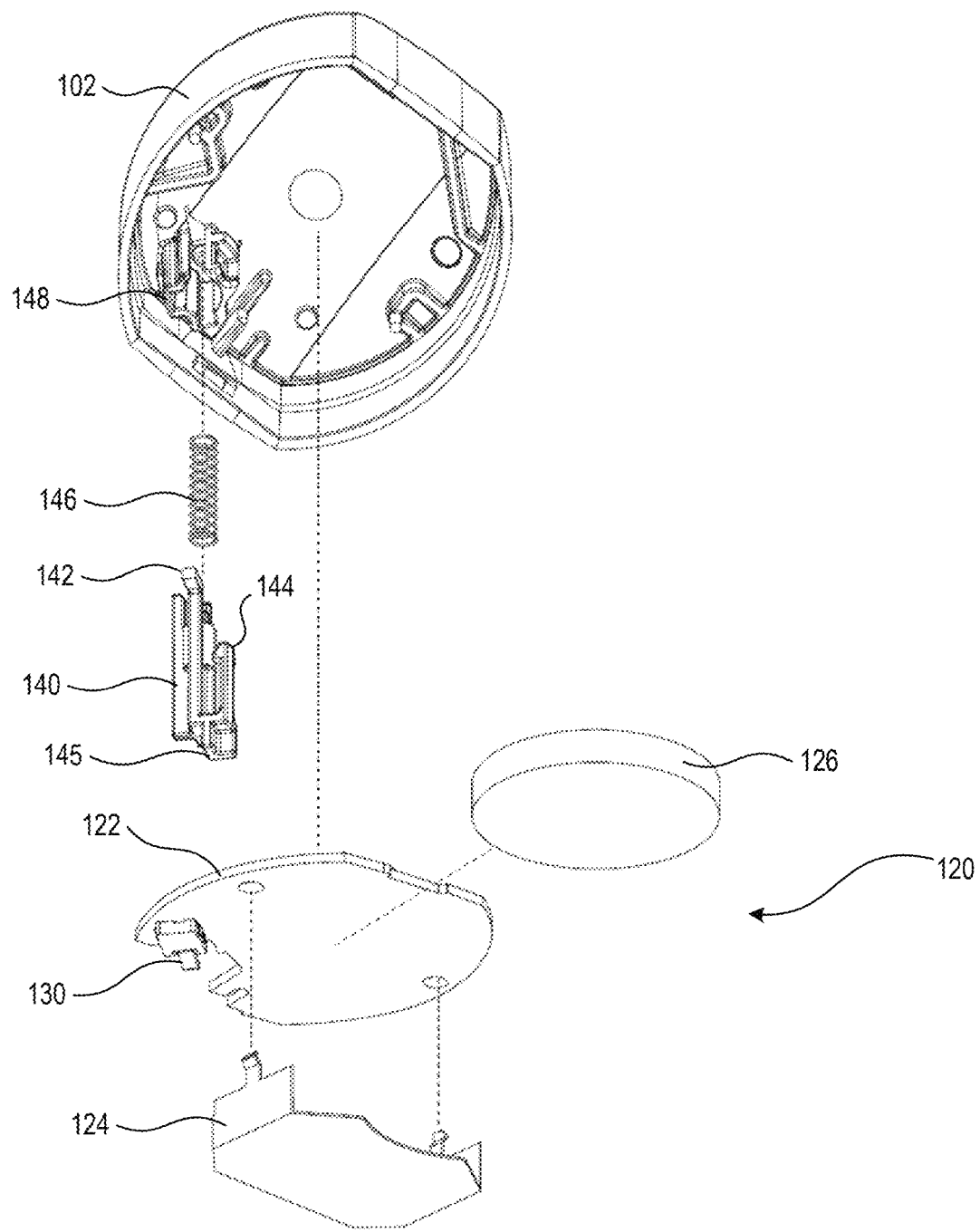
FIG. 4 is an exploded perspective view of the top cap and the electronics module of the example inhalation device of FIG. 1.

FIG. 4 is an exploded perspective view of the top cap and the electronics module of the example inhalation device 100.

The example, inhalation device 100 may be a breath-actuated inhalation device. The inhalation device 100 may include a top cap 102, a main housing 104, a mouthpiece 106, a mouthpiece cover 108, an electronics module 120, and an air vent 126. The mouthpiece cover 108 may be hinged to the main housing 104 so that it may open and close to expose the mouthpiece 106. Although illustrated as a hinged connection, the mouthpiece cover 106 may be connected to the inhalation device 100 through other types of connections. Moreover, while the electronics module 120 is illustrated as housed within the top cap 102 at the top of the main housing 104, the electronics module 120 may be integrated and/or housed within main body 104 of the inhalation device 100.

Inside the main housing 104, the inhalation device 100 may include a medication reservoir 110 (e.g., a hopper), a bellows 112, a bellows spring 114, a yoke 118, a dosing cup 116, a dosing chamber 117, a deagglomerator 121 and a flow pathway 119. The medication reservoir 110 may include medication, such as dry powder mediation, for delivery to the user. When the mouthpiece cover 108 is moved to expose the mouthpiece 106 (e.g., from a closed position to an open position), the bellows 112 may compress to deliver a dose of medication from the medication reservoir 110 to the dosing cup 116. Thereafter, a user may inhale through the mouthpiece 106 in an effort to receive the dose of medication. The airflow generated from the user's inhalation may cause the deagglomerator 121 to aerosolize the dose of medication by breaking down the agglomerates of the medicament in the dose cup 116. The deagglomerator 121 may be configured to aerosolize the medication when the airflow through the flow pathway 119 meets or exceeds a particular rate, or is within a specific range. When aerosolized, the dose of medication may travel from the dosing cup 116, into the dosing chamber 117, through the flow pathway 119, and out of the mouthpiece 106 to the user. If the airflow through the flow pathway 119 does not meet or exceed a particular rate, or is not within a specific range, some or all of the medication may remain in the dosing cup 116. In the event that the medication in the dosing cup 116 has not been aerosolized by the deagglomerator 121, another dose of medication may not be delivered from the medication reservoir 110 when the mouthpiece cover 108 is subsequently opened. Thus, a single dose of medication may remain in the dosing cup until the dose has been aerosolized by the deagglomerator 121.

As the user inhales through the mouthpiece 106, air may enter the air vent 126 to provide a flow of air for delivery of the medication to the user. The flow pathway 119 may extend from the dosing chamber 117 to the end of the mouthpiece 106, and include the dosing chamber 117 and the internal portions of the mouthpiece 106. The dosing cup 116 may reside within or adjacent to the dosing chamber 117. Further, the inhalation device 100 may include a dose counter 111 that is configured to be initially set to a number of total doses of medication within the medication reservoir 110 and to decrease by one each time the mouthpiece cover 108 is moved from the closed position to the open position.

The top cap 102 may be attached to the main housing 104. For example, the top cap 102 may be attached to the main housing 104 through the use of one or more clips that engage recesses on the main housing 104. The top cap 102 may overlap a portion of the main housing 104 when connected, for example, such that a substantially pneumatic seal exists between the top cap 102 and the main housing 104. The top surface of the main housing 104 may include one or more (e.g., two) orifices 147. One of the orifices 147 may be configured to accept a slider 140. For example, when the top cap 102 is attached to the main housing 104, the slider 140 may protrude through the top surface of the main housing 104 via one of the orifices 147.

The slider 140 may define an arm 142, a stopper 144, and a distal base 145. The distal end 145 may be a bottom portion of the slider 140. The distal end 145 of the slider 140 may be configured to abut the yoke 118 that resides within the main housing 104 (e.g., and the mouthpiece cover 108 is in the closed or partially open position). The distal end 145 may be configured to abut a top surface of the yoke 118 when the yoke 118 is in any radial orientation. For example, the top surface of the yoke 118 may include a plurality of apertures (not shown), and the distal end 145 of the slider 140 may be configured to abut the top surface of the yoke 118, for example, whether or not one of the apertures is in alignment with the slider 140.

The top cap 102 may include a slider guide 148 that is configured to receive a slider spring 146 and the slider 140. The slider spring 146 may reside within the slider guide 148. The slider spring 146 may engage an inner surface of the top cap 102, and the slider spring 146 may engage (e.g., abut) an upper portion (e.g., a proximate end) of the slider 140. When the slider 140 is installed within the slider guide 148, the slider spring 146 may be partially compressed between the top of the slider 140 and the inner surface of the top cap 102. For example, the slider spring 146 may be configured such that the distal end 145 of the slider 140 remains in contact with the yoke 118 when the mouthpiece cover 108 is closed. The distal end 145 of the slider 145 may also remain in contact with the yoke 118 while the mouthpiece cover 108 is being opened or closed. The stopper 144 of the slider 140 may engage a stopper of the slider guide 148, for example, such that the slider 140 is retained within the slider guide 148 through the opening and closing of the mouthpiece cover 108, and vice versa. The stopper 144 and the slider guide 148 may be configured to limit the vertical (e.g., axial) travel of the slider 140. This limit may be less than the vertical travel of the yoke 118. Thus, as the mouthpiece cover 108 is moved to an open position, the yoke 118 may continue to move in a vertical direction towards the mouthpiece 106 but the stopper 144 may stop the vertical travel of the slider 140 such that the distal end 145 of the slider 140 may no longer be in contact with the yoke 118.

The electronics module 120 may include a printed circuit board (PCB) assembly 122, a switch 130, a power supply (e.g., a battery 126), and/or a battery holder 124. The PCB assembly 122 may include may include surface mounted components, such as a sensor system 128, a wireless communication circuit 129, the switch 130, and or one or more indicators (not shown), such as one or more light emitting diodes (LEDs). The electronics module 120 may include a controller (e.g., a processor) and/or memory. The controller and/or memory may be physically distinct components of the PCB 122. Alternatively, the controller and memory may be part of another chipset mounted on the PCB 122. For example, the wireless communication circuit 129 may include the controller and/or memory for the electronics module 120. The controller of the electronics module 120 may include a microcontroller, a programmable logic device (PLD), a microprocessor, an application specific integrated circuit (ASIC), a field-programmable gate array (FPGA), or any suitable processing device or control circuit.

The controller may access information from, and store data in the memory. The memory may include any type of suitable memory, such as non-removable memory and/or removable memory. The non-removable memory may include random-access memory (RAM), read-only memory (ROM), a hard disk, or any other type of memory storage device. The removable memory may include a subscriber identity module (SIM) card, a memory stick, a secure digital (SD) memory card, and the like. The memory may be internal to the controller. The controller may also access data from, and store data in, memory that is not physically located within the electronics module 120, such as on a server or a smartphone.

The sensor system 128 may include one or more sensors, including, for example, one or more pressure sensors. The one or more pressure sensors may include a barometric pressure sensor (e.g., an atmospheric pressure sensor), a differential pressure sensor, an absolute pressure sensor, and/or the like. The sensors may employ microelectromechanical systems (MEMS) and/or nanoelectromechanical systems (NEMS) technology. The sensor system 128 may be configured to provide an instantaneous pressure reading to the controller of the electronics module 120 and/or aggregated pressure readings over time. As illustrated in FIGS. 2 and 3, the sensor system 128 may reside within the inhalation device 100 but remain outside of the flow pathway 119. Accordingly, the sensor system 128 may be configured to measure a plurality of atmospheric pressures within the inhalation device 100.

It will be appreciated that the atmospheric pressure within the device 100 (e.g., within the top cap 102 or within the housing 104) may be the same as or similar to the atmospheric pressure outside the device 100 when the device 100 is not being used. However, when a user inhales from the mouthpiece 106, the user's inhalation may cause the atmospheric pressure within the device 100 to decrease. Conversely, an exhalation into the mouthpiece 106 may cause the atmospheric pressure within the device 100 to increase. In both cases, the atmospheric pressure within the device 100 may differ from the atmospheric pressure outside of the device 100. Accordingly, certain parameters or metrics associated with the inhalation or exhalation may be determined by comparing changes in atmospheric pressure resulting from the inhalation or exhalation.

Figure 7:
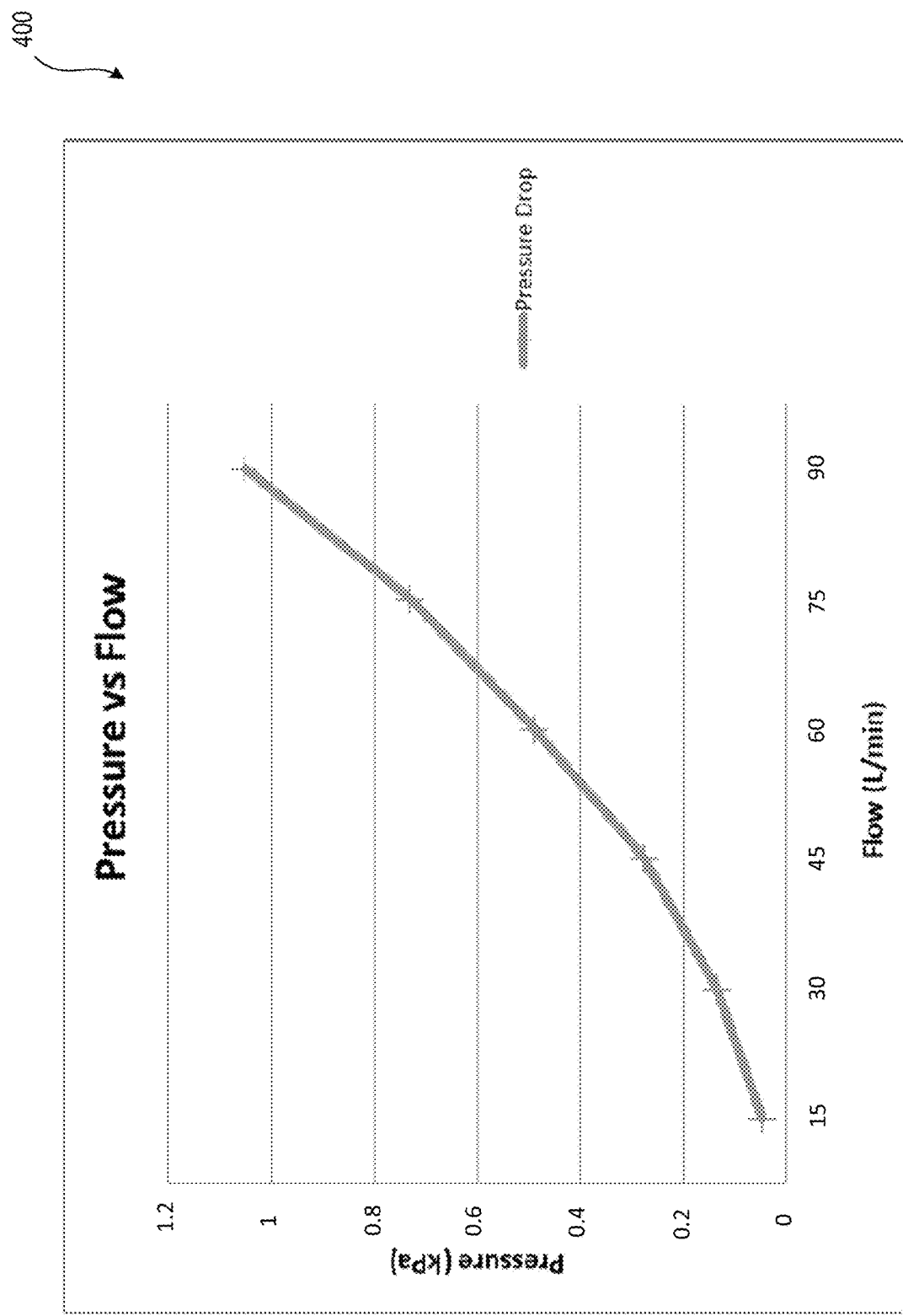
FIG. 7 is a graph of exemplary airflow rates through the example inhalation device of FIG. 1 based on pressure measurements recorded by the electronics module.

The controller of the electronics module 120 may receive signals corresponding to pressure measurements from the sensor system 128. The controller may calculate or determine one or more airflow metrics (e.g., a peak flow rate, a time to peak flow rate, an inhaled volume, an inhalation duration, etc.) using the signals received from the sensor system 128. The airflow metrics may be indicative of a profile of airflow through the flow pathway 119 of the inhalation device 100. For example, if the sensor system 128 records a change in pressure of 0.3 kilopascals (kPA), the electronics module 120 may determine that the change corresponds to an airflow rate of approximately 45 liters per minute (Lpm) through the flow pathway 119. FIG. 7 shows an example of airflow rates based on various pressure measurements. It will be appreciated that the airflow rates and profile shown in FIG. 7 are merely examples and that determined rates may depend on the size, shape, and design of the inhalation device 100 and its internal components.

The airflow metrics may include one or more of an average flow of an inhalation/exhalation, a peak flow of an inhalation/exhalation (e.g., a maximum inhalation achieved), a volume of an inhalation/exhalation, a time to peak of an inhalation/exhalation, and/or the duration of an inhalation/exhalation. The airflow metrics may also be indicative of the direction of flow through the flow pathway 119. That is, a negative change in pressure may correspond to an inhalation from the mouthpiece 106, while a positive change in pressure may correspond to an exhalation into the mouthpiece 106. When calculating the airflow metrics, the electronics module 120 may be configured to eliminate or minimize any distortions caused by environmental conditions. For example, the electronics module 120 may "zero out" to account for changes in atmospheric pressure before and/or after calculating the airflow metrics. The one or more pressure measurements and/or airflow metrics may be time-stamped and stored in the memory of the electronics module 120.

The controller of the electronics module 120 may compare signals received from the sensor system 128 and/or the determined airflow metrics to one or more thresholds or ranges, for example, as part of an assessment of how the inhalation device 100 is being used and/or whether the use is likely to result in the delivery of a full dose of medication. For example, where the determined airflow metric corresponds to an inhalation with an airflow rate below a particular threshold, the electronics module 120 may determine that there has been no inhalation or an insufficient inhalation from the mouthpiece 106 of the inhalation device 100. If the determined airflow metric corresponds to an inhalation with an airflow rate above a particular threshold, the electronics module 120 may determine that there has been an excessive inhalation from the mouthpiece 106. If the determined airflow metric corresponds to an inhalation with an airflow rate within a particular range, the electronics module 120 may determine that the inhalation is "good", or likely to result in a full dose of medication being delivered. As noted above, the electronics module 120 may include indicators, such as an LED. The indicators may be configured to provide feedback to users regarding their use of the inhalation device 100. Thus, in one example, an LED may illuminate or change color if the airflow metrics correspond to a good inhalation or to no inhalation. The airflow metrics may be computed and/or assessed via external devices as well (e.g., partially or entirely).

More specifically, the wireless communication circuit 129 in the electronics module 120 may include a transmitter and/or receiver (e.g., a transceiver), as well as additional circuitry. For example, the wireless communication circuit 129 may include a Bluetooth chip set (e.g., a Bluetooth Low Energy chip set), a ZigBee chipset, a Thread chipset, etc. As such, the electronics module 120 may wirelessly provide data such as pressure measurements, airflow metrics and/or other conditions related to usage of the inhalation device 100, to an external device, including a smartphone. The external device may include software for processing the received information and for providing compliance and adherence feedback to users of the inhalation device 100 via a graphical user interface (GUI).

The battery 126 may provide power to the components of the PCB 122. The battery 126 may be any suitable source for powering the electronics module 120, such as a coin cell battery, for example. The battery 126 may be rechargeable or non-rechargeable. The battery 126 may be housed by the battery holder 124. The battery holder 124 may be secured to the PCB 122 such that the battery 126 maintains continuous contact with the PCB 122 and/or is in electrical connection with the components of the PCB 122. The battery 126 may have a particular battery capacity that may affect the life of the battery 126. As will be further discussed below, the distribution of power from the battery 126 to the one or more components of the PCB 122 may be managed to ensure the battery 126 can power the electronics module 120 over the useful life of the inhalation device 100 and/or the medication contained therein.

The electronics module 120 may have a plurality of power states, each with respective power consumption levels. For example, the electronics module 120 may be configured to operate in a system off state, a sleep state, and/or an active state. The system off state may be characterized by very little or no power consumption, while the sleep state may be characterized by greater power consumption than the off state, and the active state may be characterized by greater power consumption than the sleep state. While the electronics module 120 is in the active state, the electronics module may operate in one or more modes, such as a measurement mode, a data storage/data processing mode, an advertising mode, and/or a connected mode. It should be appreciated that the electronics module 120 may operate in multiple modes at one time (e.g., the modes may overlap). For example, as described in more detail below, the electronics modules 120 may operate in the measurement mode and the data storage/data processing mode at discrete times or simultaneously. That is, the electronics module 120 may be perform all of the measurements prior to processing/storing the data, or the electronics module 120 may perform data processing/storage while at the same time also performing additional measurements (e.g., the electronics modules 120 may switch between the measurement mode and the data storage/data processing mode before either is complete).

In the system off state, the electronics module 120 may consume the least amount of power as compared to the other power states (e.g., the sleep state and the active state). In particular, the electronics module 120 may use a minimal amount of power to monitor a certain pin (or pins) on the controller but other components, such as the sensor system 128, the wireless communications circuit 129 (e.g., the Bluetooth radio) and memory may be powered off. The pin on the controller may be in electrical connection with the switch 130 such that actuation of the switch 130 may result in a certain reference signal on the pin. The reference signal may trigger the controller to transition from the system off state.

The system off state may be the initial state of the electronics module 120 after the inhalation device 100 is assembled or manufactured. Thus, the electronics module 120 may be in a system off state prior to the device 100 being delivered to the user and/or prior to the mouthpiece cover 108 being opened for a first time (e.g., before the first use of the inhalation device 100 by the user). In addition, once the mouthpiece cover 108 has been opened for the first time, the electronics module 120 may not return to the system off state thereafter. In some examples, the controller may start its internal clock (e.g., an internal counter) when the electronics module 120 first exits the off state, and any timestamp data generated by the electronics module 120 may be a relative time based on internal clock of the controller. Accordingly, the internal clock may act as a counter that starts when the electronics module 120 exits the off state. Alternatively or additionally, the controller may include an internal system clock that knows the actual time (e.g., 4:05 pm EST on Nov. 18, 2017) and the timestamp data may include the actual time. In such examples, the controller may use power in the off state to run its real-time clock oscillator and to update its system clock.

As noted above, while the electronics module 120 is the active state, the electronics module 120 may operate in one or more modes, such as a measurement mode, a data storage/data processing mode, an advertising mode, and/or a connected mode. In the sleep state, the switch 130 and the controller may continue to receive power from the battery 126, and the controller may continue to run its oscillator and periodically update its system clock (e.g., continue to increment the internal counter that was started when the electronics module 120 first exited the off state). In some examples, the controller may periodically update the system clock every 250 µs.

Further, while in the sleep state, the controller may receive power from the battery to control one or more additional components of the electronics module 120. For example, during the advertising mode, the controller may periodically power on the communications circuit 129 to wirelessly "advertise" to an external device that data is stored on the inhalation device 100 and is available for wireless download. The communications circuit 129 may transmit advertising packets at any interval that is suitable for managing the power consumption of the electronics module 120 when in the sleep state (e.g., as compared to the interval at which packets may be sent during the active state). For example, advertising packets may be transmitted every 10 seconds when the electronics module 120 is operating in the sleep state. It will be appreciated that the electronics module 120 may spend more time in the sleep state than in any of the other power states. Thus, at a given advertising rate, the electronics module 120 may consume the most power in the sleep state over the life of the inhalation device 100.

In the measurement mode, the controller of the electronics module 120 may power on the sensor system 128. The controller may cause the sensor system 128 to take pressure measurement readings for a predetermined time period (e.g., up to 60 seconds) and/or until the mouthpiece cover 108 is closed or no changes in pressure are detected. The controller may turn off one or more components of the electronics module 120 while the sensor system 128 is capturing pressure measurement readings to further conserve power. The sensor system 128 may sample the pressure at any suitable rate. For example, the sensor system 128 may have a sample rate of 100 Hz and thus a cycle time of 10 milliseconds. The sensor system 128 may generate a measurement complete interrupt after the measurement cycle is complete. The interrupt may "wake" the controller or cause it to turn on one or more components of the electronics module 120. For example, after or while the sensor system 128 is sampling pressure measurements, the controller may process and/or store the pressure measurement data and, if measurements are complete, power off the sensor system 128.

In the data storage/data processing mode, the controller may power on at least a portion of the memory within the electronics module 120. The controller may process the readings from the sensor system 128 to determine airflow metrics and store the airflow metrics in memory. The controller may also compare the readings and/or the airflow metrics to one or more thresholds or ranges to assess how the inhalation device is being used (e.g., whether the pressure readings correspond to no inhalation, a "good" inhalation, to an exhalation, etc.). Depending on the results of the comparison, the controller may drive the indicators to provide feedback to the user of the inhalation device 100. As noted above, the electronics module 120 may operate in the measurement mode and the data storage/data processing mode simultaneously.

In the advertising mode, the controller may power on the communication circuit 129 (e.g., the Bluetooth radio) to advertise to an external device that data is available from the inhalation device 100 and is ready for wireless download.

Advertising packets may be transmitted at any interval and for any duration that is suitable for managing the power consumption of the electronics module 120 when in the advertising mode. For example, the communications circuit 129 may transmit advertising packets every 100 milliseconds (ms) for 3 minutes. Further, it should be appreciated that the advertising rate may vary based on the particular conditions of the electronics module 120. For example, the advertising rate may be "slow" (e.g., packets are transmitted every 10 seconds) when the electronics module 120 is transitioning from the sleep state and without the mouthpiece cover 108 moving to the open position, whereas the advertising rate may be "fast" (e.g., packets are transmitted every 100 ms) after the measurements and data processing/storage has occurred.

In the connected mode, the communication circuit and memory may be powered on and the electronics module 120 may be "paired" with an external device, such as a smartphone. The controller may retrieve data from the memory and wirelessly transmit the data to the external device. The controller may retrieve and transmit all of the data currently stored in the memory. The controller may also retrieve and transmit a portion of the data currently stored in the memory. For example, the controller may be able to determine which portions have already been transmitted to the external device and then transmit the portion(s) that have not been previously transmitted. Alternatively, the external device may request specific data from the controller, such as any data that has been collected by the electronics module 120 after a particular time or after the last transmission to the external device. The controller may retrieve the specific data, if any, from the memory and transmit the specific data to the external device.

Figure 6A:
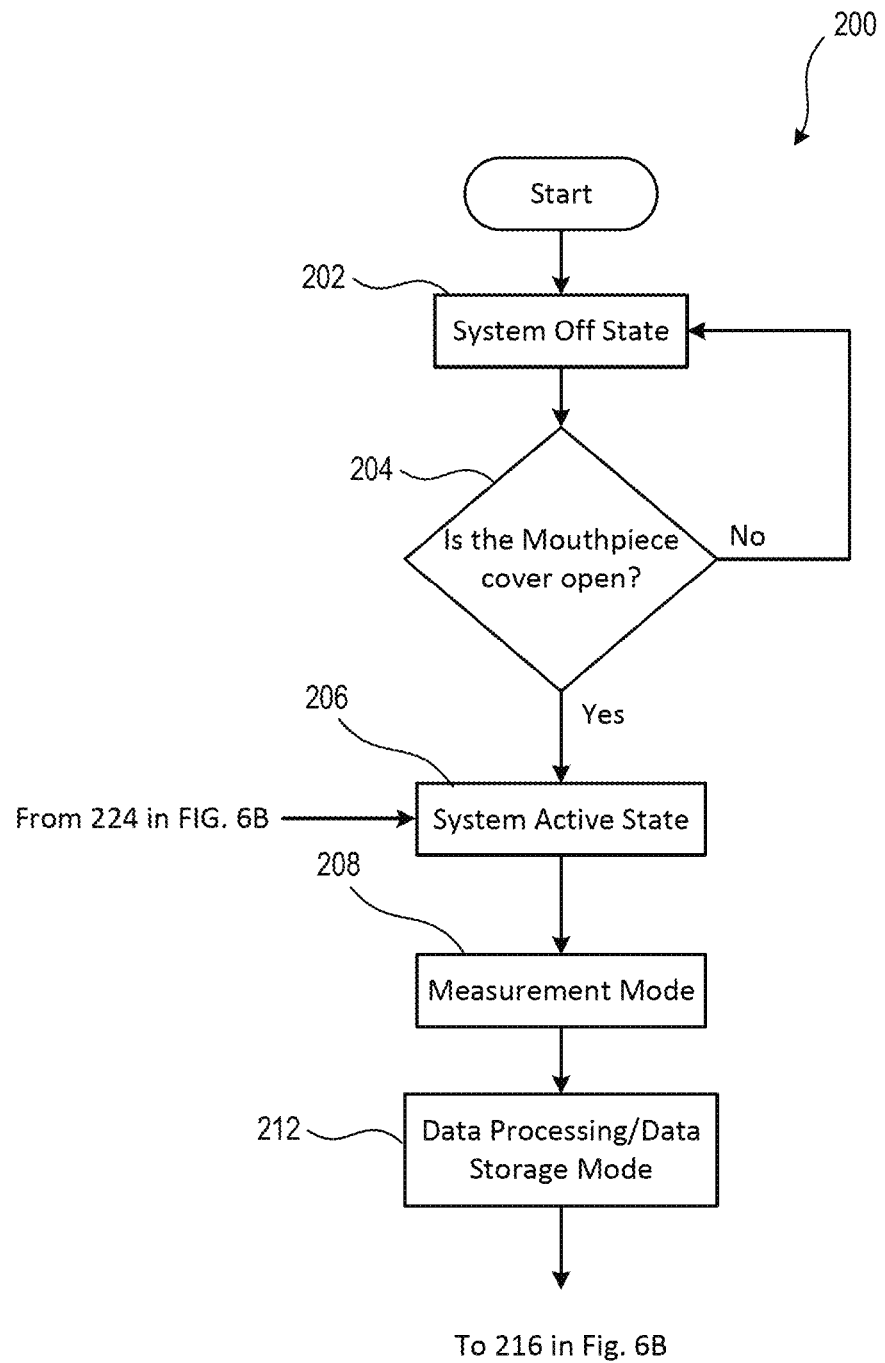
FIGS. 6A and 6B include a flow diagram that illustrates an example process for transitioning between one or more power states and/or operational modes associated with the inhalation device.
Figure 6B:
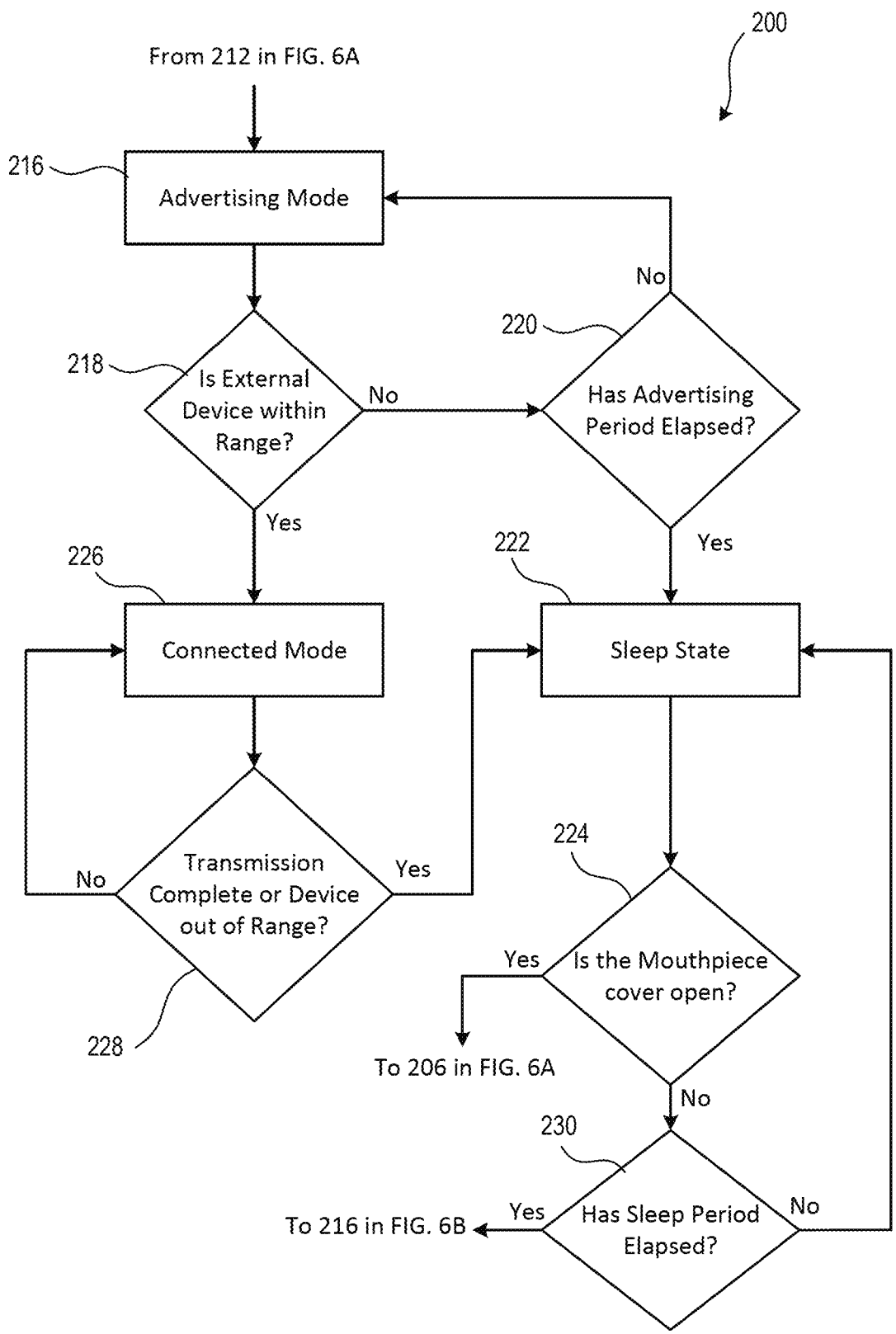

The electronics module 120 may transition between power states or operational modes based on certain conditions or events, such as the position of the mouthpiece cover 108 and/or the elapse of predetermined time periods. For example, the mouthpiece cover 108 may be closed and the electronics module 120 may be in a system off state or a sleep state. As the mouthpiece cover 108 is moved from the closed position to an open position, the switch 130 may be actuated. The actuation of the switch 130 may cause the electronics module 120 to transition from one state (e.g., the system off state or sleep state) to another state (e.g., the active state). Further, as the actuation of the switch 130 may cause the electronics module 120 to begin operating in one or more operational modes, such as the measurement mode and/or the data storage/data processing mode. For example, FIG. 6A-B illustrate an example flow diagram 200 that illustrates an example process for transitioning between one or more power states and/or operational modes associated with the inhalation device 100.

Further, it should be appreciated that the electronics module 120 may be in the system off state prior to the mouthpiece cover 108 being opened by a user for a first time (e.g., the initial opening of the mouthpiece cover 108 by the user after removing the inhalation device 100 from its packaging). Thereafter, if the mouthpiece cover 108 is returned to the closed state, the electronics module 120 will be in the sleep state (as opposed to the off state). As the user continues to use the inhalation device 100, the electronics module 120 will switch between the sleep state and the active state, based on, for example, one or more events (e.g., an opening/closing of the mouthpiece cover 108, the expiration of a timeout period, the detection of pressure measurements that exceed a threshold (e.g., are indicative of user inhalation), advertising to an external device, etc.).

Figure 5A:
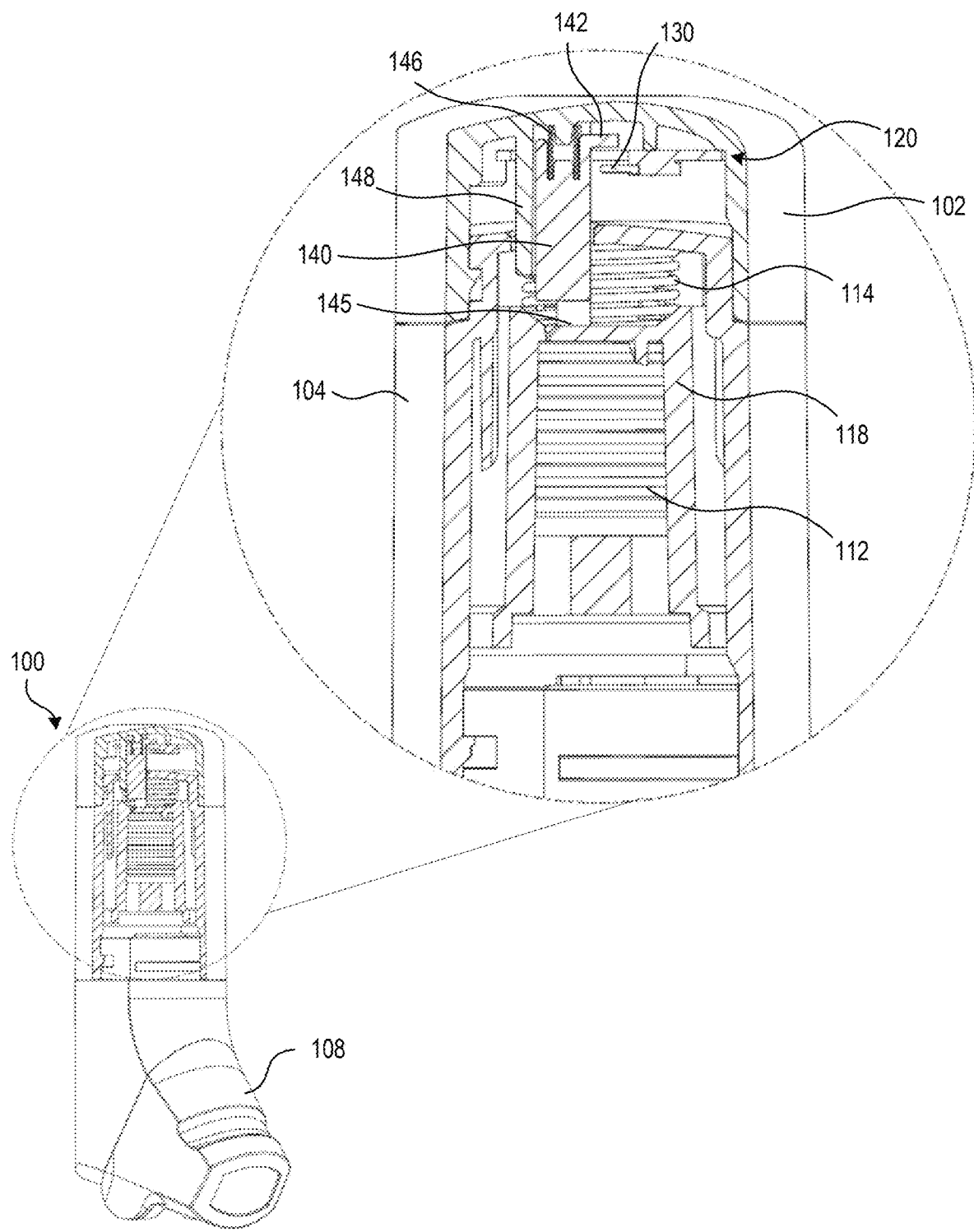
FIG. 5A is a partial cross-sectional view of the example inhalation device of FIG. 1 with a mouthpiece cover of the inhalation device in a closed position.
Figure 5B:
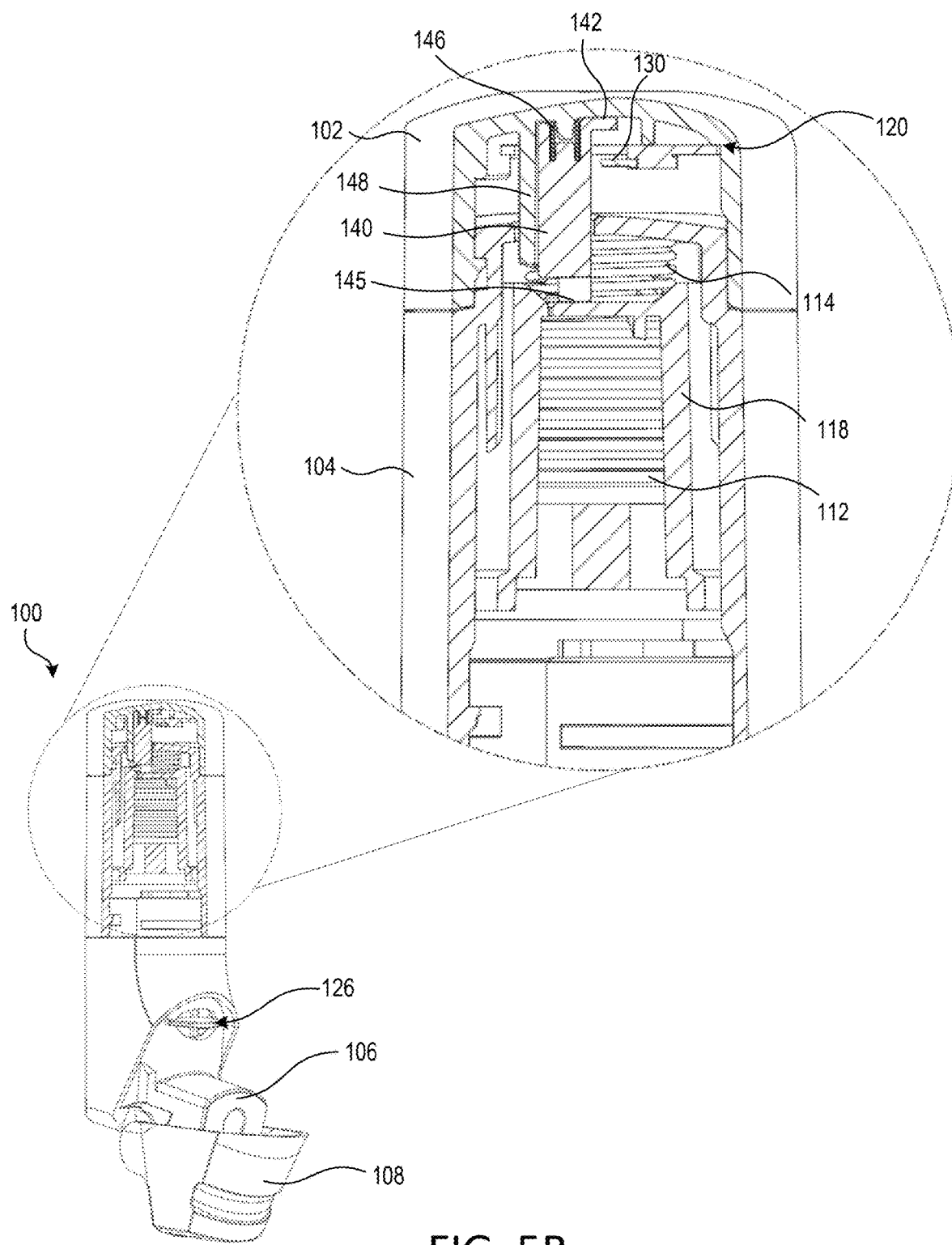
FIG. 5B is a partial cross-sectional view of the example inhalation device of FIG. 1 with the mouthpiece cover of the inhalation device in a partially open position.

FIG. 5A-5D describe one example of the internal operation of an inhalation device 100. It should be appreciated that other examples of the inhalation device 100 may include a subset of the actions described herein. Referring to FIG. 5A, the distal end 145 of the slider 140 may be configured to abut the yoke 118 that resides within the main housing 104. When the mouthpiece cover 108 is in the closed position, the arm 142 of the slider 140 may not be in contact with the switch 130. Further, the slider spring 146 and the bellows spring 114 may be in a compressed state. As the user begins to open the mouthpiece cover 108 to expose the mouthpiece 106, the yoke 118 may move upward in the main housing 104, for example, due to a mechanical connection between the yoke 118 and the mouthpiece cover 108. The upward movement of the yoke 118 may cause the slider 140 to move upward within the top cap 102, further compressing the slider spring 146 and the bellows spring 114, for example, as shown in FIG. 5B.

Figure 5C:
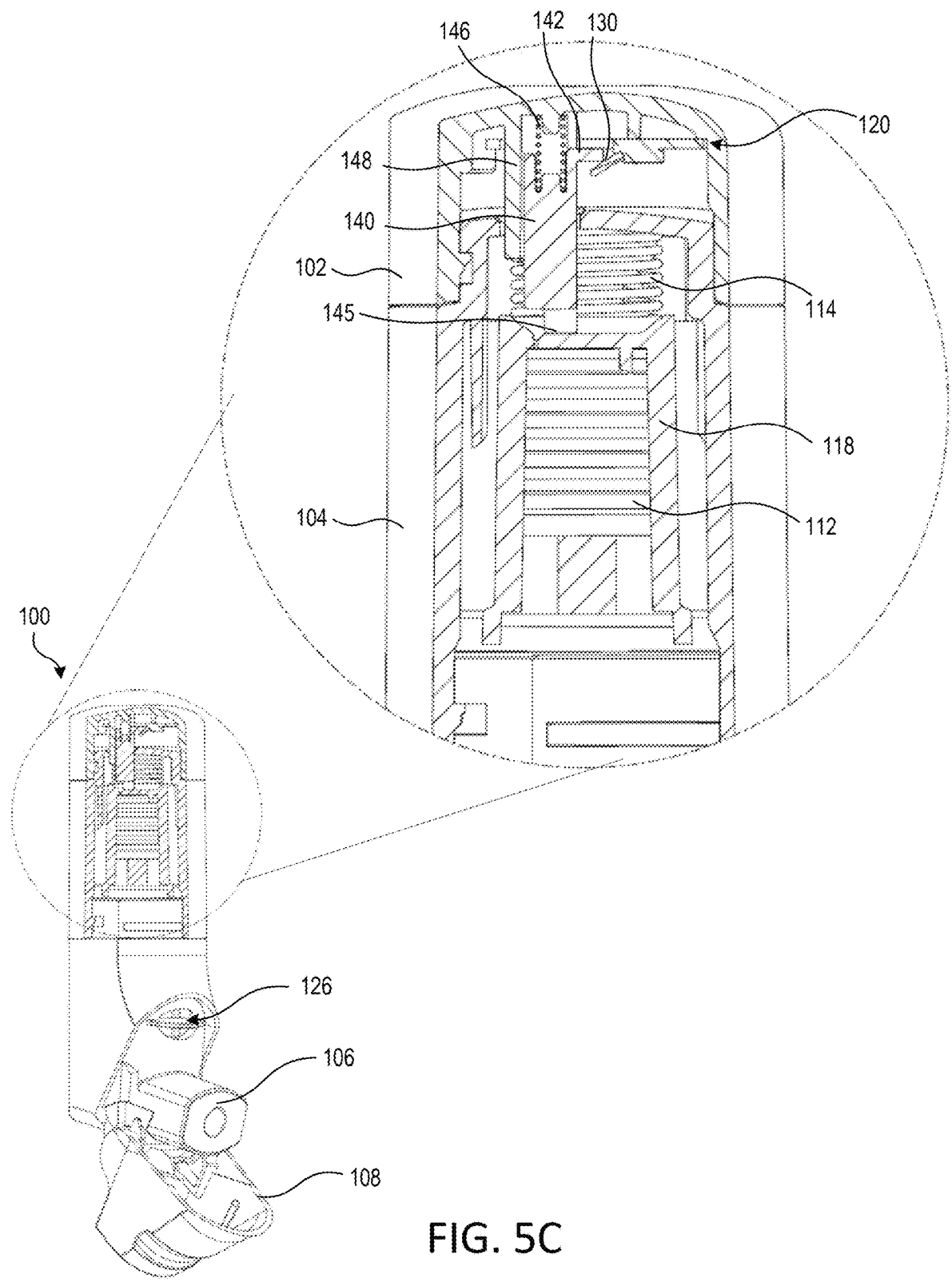
FIG. 5C is a partial cross-sectional view of the example inhalation device of FIG. 1 with the mouthpiece cover of the inhalation device in a partially open position.

As the mouthpiece cover 108 continues to move toward the fully open state, for example as shown in FIG. 5C, the mouthpiece cover 108 may cause the yoke 118 to drop within the main housing 104 (e.g., due to the downward force applied by the bellows spring 114). The movement of the yoke 118 may cause the slider 140 to drop (e.g., due to the downward force applied by the slider spring 146), which may cause the arm 142 of the slider 140 to engage the switch 130 and begin to actuate the switch 130. The downward movement of the slider 140 may be limited by the position of the yoke 118 as the distal end 145 of the slider 140 may rest upon the top of the yoke 118.

Figure 5D:
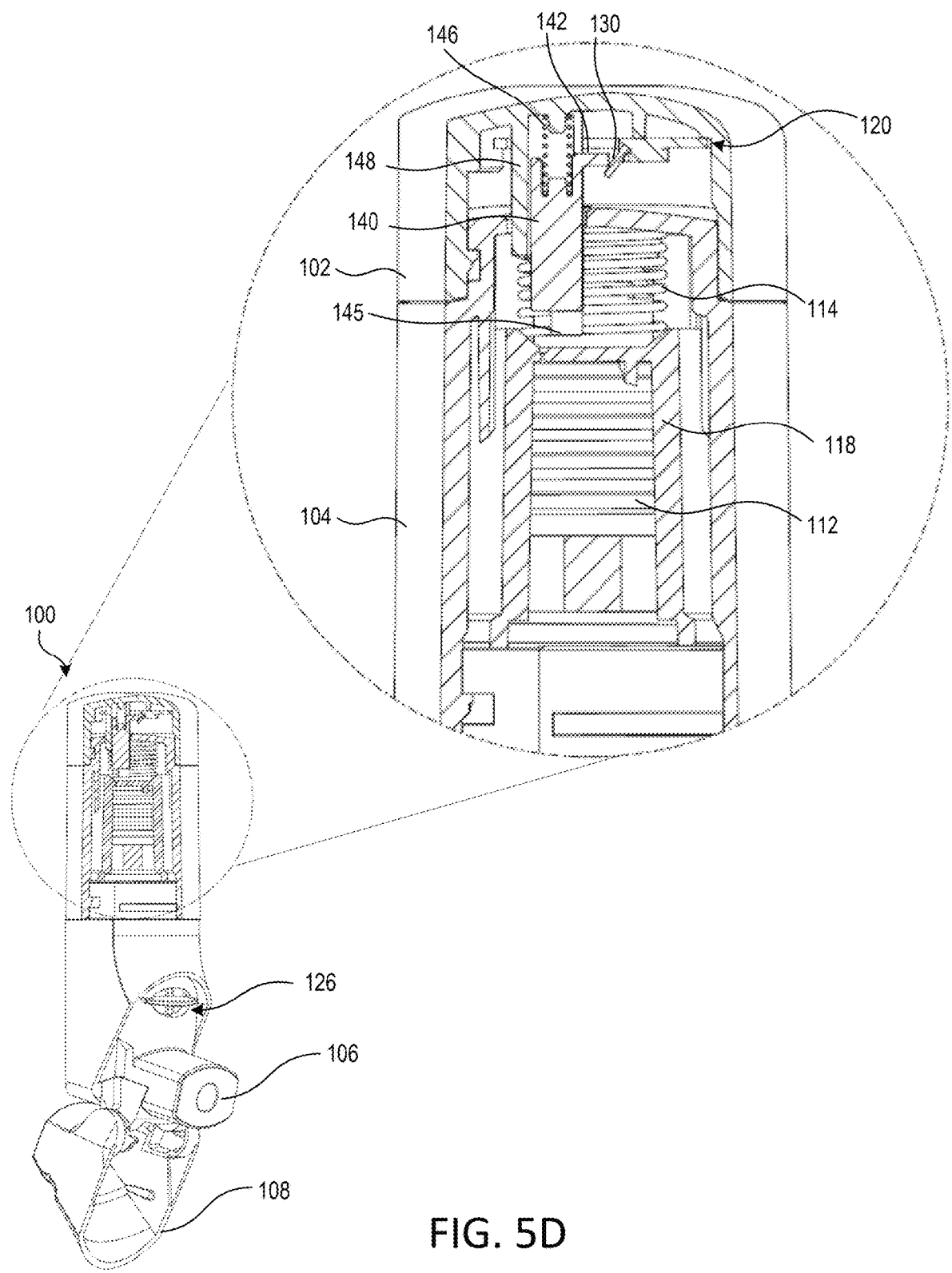
FIG. 5D is a partial cross-sectional view of the example inhalation device of FIG. 1 with the mouthpiece cover of the inhalation device in a fully open position.

As the mouthpiece cover 108 continues to open, as shown in FIG. 5D, the arm 142 of the slider 140 may actuate the switch 130, which may generate a signal causing the electronics module 120 to change states, such as from the off or sleep state to the active state. Thus, the controller of the electronics module 120 may wake and provide power to the sensor system 128 to enable the sensor system 128 to take pressure measurement readings. Moreover, the movement of the yoke 118 caused by the opening of the mouthpiece cover 108 may also cause the yoke 118 to compress the bellows 112 to cause a bolus of medication to be delivered from the medication reservoir 110 to the dosing cup 116, resulting in the medication being made available to the flow channel 119. The medication may be delivered from the dosing cup 116 through the flow channel and out the mouthpiece 106 when a user inhales from the mouthpiece 106.

FIG. 6A-B illustrate an example procedure 200 for transitioning between one or more power states and/or operational modes associated with the inhalation device 100. Although described with reference to the inhalation device 100, any inhalation device may perform the procedure 200. The electronics module 120 of the inhalation device 100 may be in the off state at 202, when the procedure 200 begins. The mouthpiece cover 108 may be in the closed position and the user may not have opened the mouthpiece cover 108 for the first time when the electronics module 120 is in the off state at 202. As noted herein, the off state may be characterized by little or no power consumption by the electronics module 120. At 204, the electronics module 120 may determine whether the mouthpiece cover 108 has been moved into the open position. If the electronics module 102 determines that the mouthpiece cover 108 has not been moved into the open position, then the electronics module 120 may reside in the off state at 202.

If the electronics module 120 determines that the mouthpiece cover 108 has been moved into the open position at 204, then the electronics module 120 may enter the system active state at 206. The active state may be characterized by greater power consumption than the off state (e.g. and the sleep state). When in the active state, the electronics module 120 may operate in one or more modes, such as a measurement mode, a data storage/data processing mode, an advertising mode, and/or a connected mode. For example, the opening of the mouthpiece cover 108 may cause the switch 130 to be actuated. The actuation of the switch 130 may cause the electronics module 120 to transition from the off state to the active state.

While in the active state, and after the mouthpiece cover 108 has been opened, the electronics module 120 may enter a measurement mode at 208. During the measurement mode, the electronics module 120 may power on the sensor system 128 and may cause the sensor system 128 to take pressure measurement readings for a predetermined time period (e.g., up to 60 seconds) and/or until the mouthpiece cover 108 is closed or no changes in pressure are detected.

In some examples, the electronics module 120 may remain in the measurement mode until the pressure measurement cycle is complete. The pressure measurement cycle may persist for a predetermined period of time and/or until a particular event is detected. For example, the pressure measurement cycle may persist for up to 60 seconds, even if the mouthpiece cover 108 has been closed and the slider 140 has disengaged from the switch 130. Alternatively, the pressure measurement cycle may persist for up to 60 seconds or until the mouthpiece cover 108 has been closed or until no changes in pressure are detected for 10 seconds, whichever comes first. It will be appreciated that the foregoing conditions are merely examples and that any suitable criteria can be used.

At 212, the electronics module 120 may enter the data processing/data storage mode. During the data processing/data storage mode, the electronics module 120 may power on at least a portion of the memory within the electronics module 120. The electronics module 120 may process the readings from the sensor system 128 to determine inhalation parameters/metrics and store the inhalation parameters/metrics in memory. The electronics module 120 may also compare the readings and/or the inhalation parameters/metrics to one or more thresholds or ranges to assess how the inhalation device is being used (e.g., whether the pressure readings correspond to no inhalation, a "good" inhalation, to an exhalation, etc.). Depending on the results of the comparison, the electronics module 120 may drive the indicators to provide feedback to the user of the inhalation device 100.

Although not illustrated by the procedure 200, the electronics module 120 may operate in the measurement mode and the data storage/data processing mode simultaneously. For example, the electronics module 120 may switch (e.g., periodically switch) between the measurement mode and the data processing/data storage mode. For example, after or while the electronics module 120 is receiving pressure measurements, the electronics module 120 may process and/or store the pressure measurement data.

The electronics module 120 may remain in the data storage/data processing mode for a predetermined period of time to process and store the pressure measurement readings from the sensor system 128. For example, the electronics module 120 may remain in the data storage/data processing mode for up to 60 ms. The electronics module 120 may, for example, use up to 50 ms to process and compute airflow metrics from the pressure measurement readings and up to 10 ms to store the pressure measurements and/or airflow metrics in the memory. Alternatively, the electronics module 120 may remain in the data storage/data processing mode for whatever duration it takes for the controller to process and store the pressure measurement readings and/or air flow metrics.

The electronics module 120 may enter the advertising mode at 216. For example, the electronics module 120 may enter the advertising mode after the predetermined period of time for data processing and data storage has elapsed, or after the controller has determined that such processing and storing are complete. During the advertising mode, the electronics module 120 may power on the communication circuit 129 (e.g., the Bluetooth radio) to advertise to an external device that data is available from the inhalation device 100 and is ready for wireless download. Advertising packets may be transmitted at any interval and for any duration that is suitable for managing the power consumption of the electronics module 120 when in the advertising mode. For example, the communications circuit 129 may transmit advertising packets every 100 milliseconds (ms) for 3 minutes. Further, it should be appreciated that the advertising rate may vary based on the particular conditions of the electronics module 120. For example, the advertising rate may be "slow" (e.g., packets are transmitted every 10 seconds) when the electronics module 120 is transitioning from the sleep state and without the mouthpiece cover 108 moving to the open position (e.g., when transitioning from 230 to 216), whereas the advertising rate may be "fast" (e.g., packets are transmitted every 100 ms) after the measurements and data processing/storage has occurred (e.g., when transitioning from 212 to 216).

At 218, the electronics module 120 may determine if an external device is within range. If the external device does not come within a particular range of the electronics module 120 during the advertising mode, the electronics module 120 may determine whether an advertising period (e.g., 3 minutes) has elapsed at 220. The advertising period may be a period of time that the electronics module 120 continues to advertise to an external device before changing power states. If the advertising period has not elapsed, then the electronics module 120 may continue to advertise to the external device at 216. However, if the advertising period has elapsed, then the electronics module 120 may move to a sleep state at 222. The sleep state may be characterized by greater power consumption than the off state, but less power consumption than the on state.

The electronics module 120 may remain in the sleep state for a predetermined amount of time or until the electronics module determines that the mouthpiece cover 108 has been moved from the closed to the open position. For example, the electronics module 120 may periodically switch between the sleep state and the advertising mode (e.g., the slow advertising mode) of the active state. For example, at 224, the electronics module 120 may determine whether the mouthpiece cover 108 has been moved from the closed to the open position. If the mouthpiece cover 108 has been moved into the open position, then the electronics module 120 may enter the active state at 206. For example, the opening of the mouthpiece cover 108 may cause the switch 130 to be actuated. The actuation of the switch 130 may cause the electronics module 120 to transition from the sleep state to the active state.

If the electronics module 120 determines that the mouthpiece cover 108 remains in the closed position, then the electronics module 120 may determine whether a sleep period (e.g., 10 seconds) has elapsed at 230. If the sleep period has not elapsed at 230, then the electronics module 120 may stay in the sleep state and return to 222. However, if the sleep period has elapsed at 230, then the electronics module 120 may return to the advertising mode of the active state at 216. When the electronics module 120 transitions from 230 to 216, the electronics module 120 may advertises at a different, possibly slower rate as compared to when the electronics module 120 transitions from 212 to 216 (e.g., such as once every 10 seconds as opposed to once every 100 ms). As such, the electronics module 120 may use less battery power during such advertising modes. Further, the electronics module 120 may periodically switch between the active state and the sleep state based on the advertising period and the sleep period (e.g., and while the mouthpiece cover 108 is in the closed position).

Returning to 218, if the external device (e.g., smartphone or tablet) comes within a particular range of the electronics module 120 during the advertising mode, the electronics module 120 may "pair" with the external device and enter the connected mode at 226. In the connected mode, the electronics module 120 may power on the communication circuit and memory. The electronics module 120 may retrieve data from the memory and wirelessly transmit the data to the external device. At 228, the electronics module 120 may determine whether the transmission is complete or the external device is out of communication range. If the transmission is not complete and the external device is within the communication range, then the electronics module 120 will remain in the connected mode. However, if the transmission is complete or if the external device is out of the communication range, then the electronics module 120 will transition to the sleep state at 222.

During the connected mode, the electronics module 120 may retrieve and transmit all of the data currently stored in the memory, or the controller may retrieve and transmit a portion of the data currently stored in the memory. For example, the controller may be able to determine which portions have already been transmitted to the external device and then transmit the portion(s) that have not been previously transmitted (e.g., based on the internal counter). Alternatively or additionally, the external device may request specific data from the electronics module 120, such as any data that has been collected by the electronics module 120 after a particular time or after the last transmission to the external device. The electronics module 120 may retrieve the specific data, if any, from the memory and transmit the specific data to the external device.

Further, when connected with the external device, the electronics module 120 may be configured to transmit Bluetooth special interest group (SIG) characteristics for managing access to records stored in the module 120. The Bluetooth SIG characteristics may include one or more of a manufacturer name of the inhalation device 100, a serial number of the inhalation device 100, a hardware revision number of the inhalation device 100, and/or a software revision number of the inhalation device 100. When connected with the external device, the electronics module 120 may retrieve data from memory and transmit the data to the external device.

The inhalation device 100 may transmit an inhalation event, an inhalation parameter, a pressure measurement, a mouthpiece cover 108 event, an error event, an operating characteristic of the inhalation device (e.g., remaining battery life), and/or associated timestamps (e.g., based on the internal counter) to the external device when in the connected mode. For example, the signals generated by the switch 130, the pressure measurement readings taken by the sensory system 128, and/or the airflow metrics computed by the controller of the electronics modules 120 may be time-stamped and stored in memory. The foregoing data may be indicative of various usage parameters associated with the inhalation device 100. For example, as movement of the slider 140 causes the switch 130 to transition between "on" and "off", the controller of the electronics module 120 may use the signals from the switch 130 to record and timestamp each transition. Further, as the transition of the switch 130 between "on" and "off" may correlate to the position of the mouthpiece cover 108 (e.g., open or closed), the electronics module 120 may be able to detect and track the position of the mouthpiece cover 108 over time. It will be appreciated that the electronics module 120 may be able to sense and track the status of the mouthpiece cover 108 without interfering with the delivery of medication through the flow pathway 119 of the inhalation device 100.

The pressure measurement readings and/or the computed airflow metrics may be indicative of the quality or strength of inhalation from the inhalation device 100. For example, when compared to a particular threshold or range of values, the readings and/or metrics may be used to categorize the inhalation as a certain type of event, such as a good inhalation event, a low inhalation event, a no inhalation event, or an excessive inhalation event.

The no inhalation event may be associated with pressure measurement readings and/or airflow metrics below a particular threshold, such as an airflow rate less than 30 Lpm. The no inhalation event may occur when a user does not inhale from the mouthpiece 106 after opening the mouthpiece cover 108 and during the measurement cycle. The no inhalation event may also occur when the user's inspiratory effort is insufficient to ensure proper delivery of the medication via the flow pathway 119, such as when the inspiratory effort generates insufficient airflow to activate the deagglomerator 121 and, thus, aerosolize the medication in the dosing cup 116.

The low inhalation event may be associated with pressure measurement readings and/or airflow metrics within a particular range, such as an airflow rate between 30 Lpm and 45 Lpm. The low inhalation event may occur when the user inhales from the mouthpiece 106 after opening the mouthpiece cover 108 and the user's inspiratory effort causes at least a partial dose of the medication to be delivered via the flow pathway 119. That is, the inhalation may be sufficient to activate the deagglomerator 121 such that at least a portion of the medication is aerosolized from the dosing cup 116.

The good inhalation event may be associated with pressure measurement readings and/or airflow metrics above the low inhalation event, such as an airflow rate between 45 Lpm and 200 Lpm. The good inhalation event may occur when the user inhales from the mouthpiece 106 after opening the mouthpiece cover 108 and the user's inspiratory effort is sufficient to ensure proper delivery of the medication via the flow pathway 119, such as when the inspiratory effort generates sufficient airflow to activate the deagglomerator 121 and aerosolize a full dose of medication in the dosing cup 116.

The excessive inhalation event may be associated with pressure measurement readings and/or airflow metrics above the good inhalation event, such as an airflow rate above 200 Lpm. The excessive inhalation event may occur when the user's inspiratory effort exceeds the normal operational parameters of the inhalation device 100. The excessive inhalation event may also occur if the device 100 is not properly positioned or held during use, even if the user's inspiratory effort is within a normal range. For example, the computed airflow rate may exceed 200 Lpm if the air vent 126 is blocked or obstructed (e.g., by a finger or thumb) while the user is inhaling from the mouthpiece 106.

It will be appreciated that any suitable thresholds or ranges may be used to categorize a particular event. It will further be appreciated that some or all of the events may be used. For example, the no inhalation event may be associated with an airflow rate below 45 Lpm and the good inhalation event may be associated with an airflow rate between 45 Lpm and 200 Lpm. As such, the low inhalation event may not be used at all in some cases.

The pressure measurement readings and/or the computed airflow metrics may also be indicative of the direction of flow through the flow pathway 119 of the inhalation device 100. For example, if the pressure measurement readings reflect a negative change in pressure, the readings may be indicative of air flowing out of the mouthpiece 106 via the flow pathway 119. If the pressure measurement readings reflect a positive change in pressure, the readings may be indicative of air flowing into the mouthpiece 106 via the flow pathway 119. Accordingly, the pressure measurement readings and/or airflow metrics may be used to determine whether a user is exhaling into the mouthpiece 106, which may signal that the user is not using the device 100 properly.

By timestamping and storing the signals generated by the switch 130, the pressure measurement readings taken by the sensory system 128, and/or the airflow metrics computed by the controller of the electronics module 120, the data collected and stored by the electronics module 120 may be used to determine whether the usage parameters are suitable or appropriate over a given period of time. As such, the data may be indicative of other events, such as an overuse event, an underuse event, or an optimal use event.

For example, the user of the inhalation device 100 may be prescribed by his or her doctor to take two doses of medication via the inhalation device 100 each day. In addition, the medication contained in the inhalation device 100 may also be approved (for safety and regulatory purposes) to be taken no more eight times each day. The overuse event may occur if the electronics module 120 records more than two good inhalations in a twenty-four hour period (i.e., the actual dosing is exceeding the prescribed number of doses) and/or if the electronics module 120 records more than eight good inhalations in a twenty-four hour period (i.e., the actual dosing is exceeding the regulatory approved number of doses). The underuse event may occur if the electronics module 120 records less than two good inhalations in a twenty-four hour period (i.e., the actual dosing is below the prescribed number of doses). The optimal use event may occur if the electronics module 120 records two good inhalations in a twenty-four hour period (i.e., the actual dosing is below the prescribed number of doses). It will be appreciated that optimal use events may be indicative of a user who is adherent. It will further be appreciated that the prescribed dosing schedule and/or the maximum approved dosing schedule may depend on the type of medication contained in the inhalation device 100. In addition, the events may be defined using any suitable number of doses over any suitable period of time, such as two doses per day, fourteen doses per week, 60 doses per month, etc.

The data collected and stored by the electronics module 120 may also be used to estimate the number doses that have been delivered from the inhalation device 100 and/or estimate the number of doses that remain in the medication reservoir 110. For example, each time the switch 130 is activated via the opening of the mouthpiece cover 108, the signal generated by the switch 130 may be counted as a dose delivery event. Thus, the inhalation device 100 may be deemed to have delivered 60 doses when the mouthpiece cover 108 is opened 60 times. The inhalation device 100 may be configured to store enough medication in the medication reservoir 110 to deliver a predefined total number of doses, such as a total of 200 doses. As such, the inhalation device 100 may also be deemed to have 140 doses remaining after the mouthpiece cover 108 is opened 60 times.

As noted above, medication will not be delivered from the medication reservoir 110 upon the user opening the mouthpiece cover 108 if a previous dose of medication was not properly aerosolized by the deagglomerator 121 and/or transferred from the dosing cup 116. Thus, it will be appreciated that counting the number of doses based on the opening of the mouthpiece cover 108 may not accurately reflect the actual number of doses delivered by the device 100 if, for example, a user opens and closes the mouthpiece cover 108 without inhaling from the mouthpiece 106. Accordingly, other data in the electronics module 120 may be used and/or combined with the signals from the switch 130 to determine the number of doses delivered and/or remaining in the device 100. For example, a dose may be counted as delivered each time a computed airflow metric is above a threshold or within a particular range, such as when a good inhalation event has been recorded. By calculating and tracking the number of doses delivered and/or remaining, the electronics module 120 may be configured to identify a refill event, which may be indicative of a time when a user should consider obtaining a new inhalation device 100.

The data collected and stored by the electronics module 120 may also be used to determine various error conditions associated with the operation of the module 120. For example, when processing the data the electronics module 120 may generate a bad data flag, a data corrupt flag, a timestamp error flag, and/or the like. The electronics module 120 may generate the bad data flag when the controller of the electronics module 120 determines that one or more signals received from the sensor system 128 are outside a predetermined range, which may indicate a malfunction in the sensor system 128. The electronics module 120 may generate the data corrupt flag when the controller's cyclic redundancy check (CRC) of data does not match what is stored in memory, which may indicate a malfunction of the memory and/or that the data in the memory has been corrupted. The electronics module 120 may generate a timestamp error flag when the controller loses its electrical connection with the battery 126, causing the controller's system clock to reset. If the controller's system clock is reset, the controller may restart its clock from the last stored counter value.

The electronics module 120 (e.g., and/or a mobile application residing on an external device) may also analyze the recorded events over a period of time to identify multiple error events, which may include a pattern of use indicative of a user who is not familiar with the proper operation of the inhalation device 100 and thus a user who may require further training. For example, the electronics module 120 may look at the number of good inhalation events over a predetermined period of time and/or over a predetermined number of openings of the mouthpiece cover 108. A multiple error event may occur when a user has had only two good inhalation events over the past week, or has had six or less good inhalations over the last twelve openings of the mouthpiece cover 108. It will be appreciated that the foregoing conditions are merely exemplary and that any suitable pattern of use may be used to define a multiple error event.

The data collected and stored by the electronics module 120 may also be used to assess the amount of power remaining in the battery 126. For example, the controller may determine whether there is a low battery event or condition, such as whether the battery has less than a predetermined amount of charge remaining (e.g., below 10%).

It will be appreciated that electronics module 120 may process and analyze the data stored in memory (e.g., the signals generated by the switch 130, the pressure measurement readings taken by the sensory system 128 and/or the airflow metrics computed by the controller of the PCB 122) to determine the usage parameters associated with the inhalation device 100. For example, the electronics module 120 may process the data to identify no inhalation events, low inhalations events, good inhalation events, excessive inhalation events and/or exhalation events. The electronics module 120 may also process the data to identify underuse events, overuse events and optimal use events. The electronics module 120 may further process the data to estimate the number of doses delivered and/or remaining and to identify error conditions, such as those associated with a timestamp error flag. The electronics module 120 may inform the user of some or all of the foregoing usage parameters of the inhalation device 100 using the indicators, such as one or more LEDs. As an example, the electronics module 120 may illuminate an LED to indicate a good inhalation event or change the color of an LED to indicate a low inhalation event or a no inhalation event. The usage parameters may be indicated to the user via any combination of light sequences and/or light color schemes.

It will further be appreciated that the data stored in the memory of the electronics module 120 (e.g., the signals generated by the switch 130, the pressure measurement readings taken by the sensory system 128 and/or the airflow metrics computed by the controller of the electronics module 120) may also be transmitted to an external device, which may process and analyze the data to determine the usage parameters associated with the inhalation device 100. Further, a mobile application residing on the mobile device may generate feedback for the user based on data received from the electronics module 120. For example, the mobile application may generate daily, weekly, or monthly report, provide confirmation of error events or notifications, provide instructive feedback to the user, and/or the like.

Figure 8:
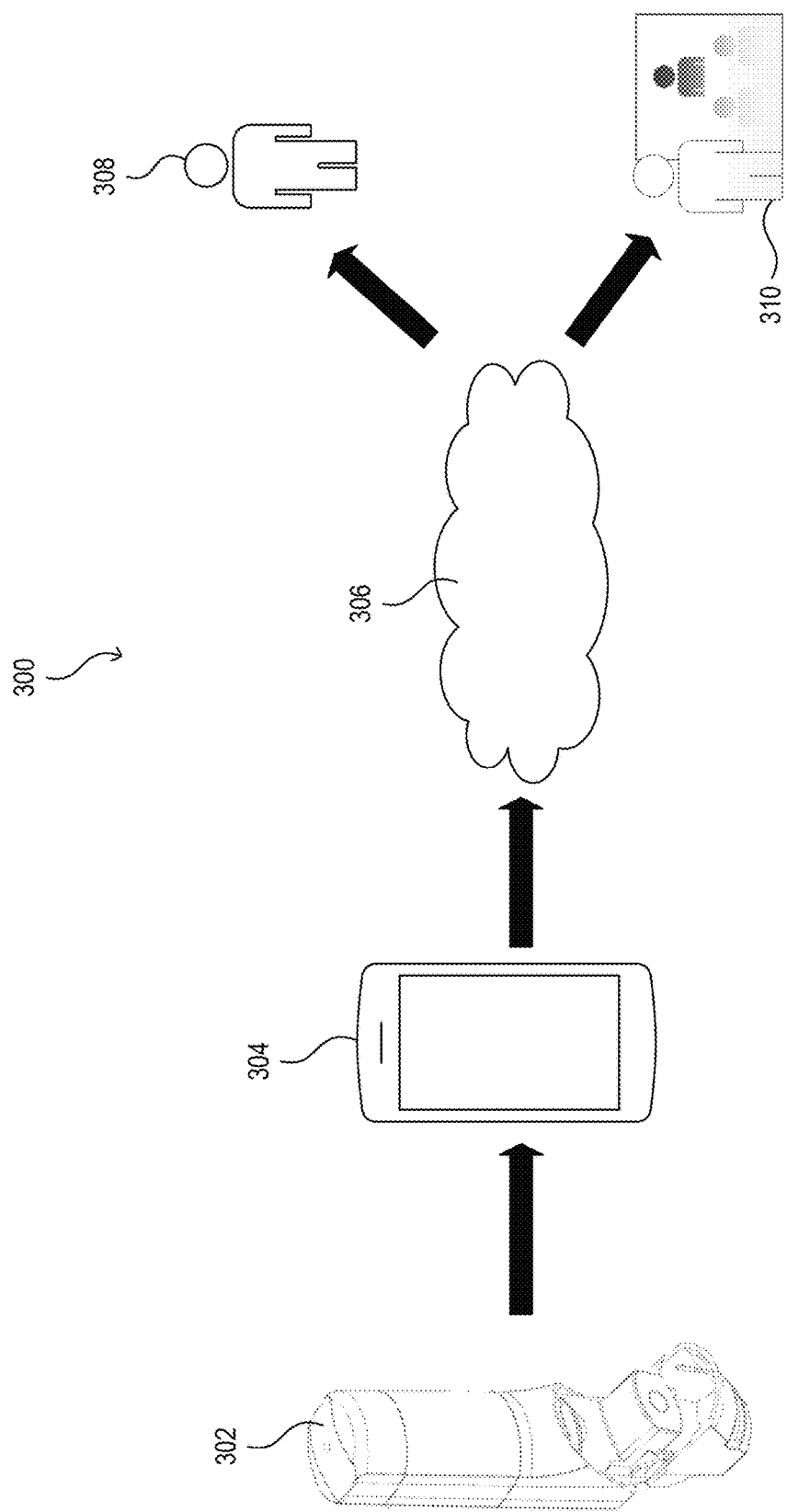
FIG. 8 is a diagram of an example system including an inhalation device.

FIG. 8 is a diagram of an example system 300 including an inhalation device 302, an external device (e.g., a mobile device 304), a public and/or private network 306 (e.g., the Internet, a cloud network), a health care provider 308, and a third party 310 (e.g., friends, family, pharmaceutical manufacturer, etc.). The mobile device 304 may include a smart phone (e.g., an iPhone® smart phone, an Android® smart phone, or a Blackberry® smart phone), a personal computer, a laptop, a wireless-capable media device (e.g., MP3 player, gaming device, television, a media streaming devices (e.g., the Amazon Fire TV, Nexus Player, etc.), etc.), a tablet device (e.g., an iPad® hand-held computing device), a Wi-Fi or wireless-communication-capable television, or any other suitable Internet-Protocol-enabled device. For example, the mobile device 304 may be configured to transmit and/or receive RF signals via a Wi-Fi communication link, a Wi-MAX communications link, a Bluetooth® or Bluetooth Smart communications link, a near field communication (NFC) link, a cellular communications link, a television white space (TVWS) communication link, or any combination thereof. The mobile device 304 may transfer data through the public and/or private network 306 to the health care provider 308 and/or one or more third parties 310 (e.g., friends, family, pharmaceutical company, etc.).

The inhalation device 302 may be an example of the inhalation device 100. The inhalation device 302 may include a communication circuit, such as a Bluetooth radio, for transferring data to the mobile device 304. The data may include the signals generated by the switch 130, the pressure measurement readings taken by the sensory system and/or the airflow metrics computed by the controller of the electronics module. The inhalation device 302 may receive data from the mobile device 304, such as, for example, program instructions, operating system changes, dosage information, alerts or notifications, acknowledgments, etc.

The mobile device 304 may process and analyze the data to determine the usage parameters associated with the inhalation device 302. For example, the mobile device 304 may process the data to identify no inhalation events, low inhalations events, good inhalation events, excessive inhalation events and/or exhalation events. The mobile device 304 may also process the data to identify underuse events, overuse events and optimal use events. The mobile device 304 may further process the data to estimate the number of doses delivered and/or remaining and to identify error conditions, such as those associated with a timestamp error flag. The mobile device 304 may include a display and software for visually presenting the usage parameters through a GUI on the display.

Further, in some examples, the inhalation device 300 may include an actuator to initiate a pairing process with the mobile device 304. However, the inhalation device 300 may include other means for facilitating the pairing process. For example, the top cap of the inhalation device 300 may include a Quick Response (QR) code. The mobile device 304 may include a camera and software application for accessing the camera and reading the QR code. The QR code may include a BLE passkey that is unique to the inhalation device 300. Upon reading or scanning the QR code using the camera, the software application may receive the BLE passkey associated with the device 300 and complete an authentication process, thereby enabling it to communicate with the electronics module using the BLE passkey. If the communications session is subsequently lost because, for example, the inhalation device 300 moves out of range, the mobile device 304 may be configured to use the BLE passkey to automatically pair with the electronics module without using the QR code when the inhalation device 300 is back within range.

What is claimed is:

1. An inhaler for delivering medication to a user, the inhaler comprising:
 a reservoir for storing the medication;
 a mouthpiece including a flow pathway through which a dose of the medication can be delivered from the reservoir to the user;
 a mouthpiece cover configured to release a dose of the medication such that the dose is available to the flow pathway for user inhalation as the mouthpiece cover is moved to expose the mouthpiece;
 an air vent coupled to the flow pathway, wherein the air vent is configured to provide a flow of air from the exterior of the inhaler to the flow pathway; and
 an electronics module comprising a controller, a pressure sensor, and a communication circuit;
 wherein the pressure sensor is configured to measure pressure changes within the inhaler resulting from an inhalation from the mouthpiece; and wherein the controller is configured to generate a mouthpiece cover opening event in response to movement of the mouthpiece cover of the inhaler from a closed position to an open position to make a dose of the medication available to the flow pathway and expose the mouthpiece, receive pressure measurement data from the pressure sensor, generate an inhalation event in response to the pressure measurement data indicating that a flow rate in the flow pathway exceeds a threshold, and cause the communication circuit to transmit the inhalation event and the mouthpiece cover opening event to an external device.

2. The inhaler of claim 1, wherein the controller is configured to generate a no inhalation error event in response to the pressure measurement data indicating that a flow rate in the flow pathway does not exceed the threshold, and cause the communication circuit to transmit the no inhalation error event to the external device.

3. The inhaler of claim 2, wherein the controller is configured to start a measurement cycle in response to movement of the mouthpiece cover from the closed position to the open position, and generate the no inhalation error event in response to the pressure measurement data indicating that the flow rate in the flow pathway does not exceed the threshold during the measurement cycle, wherein the measurement cycle persists for a predetermined period of time or until the mouthpiece cover is moved from the open position to the closed position, whichever comes first.

4. The inhaler of claim 1, wherein the pressure sensor is further configured to measure the change in pressure within the inhaler resulting from an exhalation into the mouthpiece, and the controller is configured to generate an exhalation event in response to the pressure measure data indicating a positive change in pressure that exceeds an exhalation threshold, and cause the communication circuit to transmit the exhalation event to the external device.

5. The inhaler of claim 1, wherein the mouthpiece cover opening event is indicative of a dose of the medication being delivered from the reservoir.

6. The inhaler of claim 1, further comprising:
a dose counter that is configured to decrement based on movement of the mouthpiece cover over the inhaler.

7. The inhaler of claim 1, wherein the controller is configured to determine one or more inhalation parameters based on the pressure measurement data, and cause the communication circuit to wirelessly transmit the inhalation parameters to the external device;
wherein the inhalation parameters comprise a peak flow rate, a time to peak flow rate, an inhaled volume, and an inhalation duration.

8. The inhaler of claim 1, further comprising:
a dosing chamber coupled to the flow pathway, wherein the dosing chamber is configured to deliver the dose of the medication to the flow pathway during the inhalation from the mouthpiece; and
a Quick Response (QR) code that comprises a communication passkey that is unique to the inhaler and enables wireless communication with the electronics module of the inhaler.

9. A method for detecting a usage condition of an inhaler for delivering medication using a device that comprises a mouthpiece, an air vent, a medicament reservoir, a controller, memory, a sensor, and a communication circuit, the method comprising:
in response to movement of a mouthpiece cover of the inhaler from a closed position to an open position:
generating a mouthpiece cover opening event;
releasing a dose of the medication from the medicament reservoir such that the dose is available to a flow pathway of the inhaler as the mouthpiece cover is moved to expose the mouthpiece; and
causing the controller to power on the sensor;
measuring a change in pressure within the inhaler resulting from an inhalation from the mouthpiece, wherein the inhalation causes a flow of air to travel along the flow pathway of the inhaler between the mouthpiece and the air vent;
determining an airflow rate through the flow pathway based on the change of pressure within the inhaler;
generating an inhalation event based on the airflow rate exceeding a threshold; and
transmitting the mouthpiece cover opening event and the inhalation event to an external device.

10. The method of claim 9, further comprising:
determining that the airflow rate exceeds the threshold;
generating an excessive inhalation event in response to the airflow rate exceeding the threshold; and
displaying a notification of the excessive inhalation event.

11. The method of claim 10, wherein the notification of the excessive inhalation event indicates that the air vent of the inhaler has been blocked or obstructed.

12. The method of claim 9, further comprising measuring a positive change in pressure within the inhaler resulting from an exhalation into the mouthpiece, generating an exhalation event based on the positive change in pressure exceeding an exhalation threshold, and transmitting the exhalation inhalation event to the external device.

13. The method of claim 9, further comprising:
starting a measurement cycle in response to movement of the mouthpiece cover from the closed position to the open position;
generating a no inhalation event based on the airflow rate not exceeding the threshold during the measurement cycle, wherein the measurement cycle persists for a predetermined period of time or until the mouthpiece cover is moved from the open position to the closed position, whichever comes first; and
transmitting the no inhalation event to the external device.

14. A system for detecting a usage condition of an inhaler for delivering medication, the system comprising:
an inhaler comprising:
a reservoir for storing the medication;
a mouthpiece including a flow pathway through which a dose of the medication is configured to be delivered from the reservoir to a user; a mouthpiece cover configured to release a dose of the medication such that the dose is available to the flow pathway for user inhalation as the mouthpiece cover is moved to expose the mouthpiece; an
air vent coupled to the flow pathway, wherein the air vent is configured to facilitate a flow of air from the exterior of the inhaler to the flow pathway; and
an electronics module comprising a controller, a pressure sensor, and a communication circuit;
wherein the pressure sensor is configured to measure a change in pressure within the inhaler resulting from an inhalation from the mouthpiece; and
wherein the controller is configured to:
receive pressure measurement data from the pressure sensor,
determining an airflow rate through the flow pathway based on the pressure measurement data;
generate an inhalation event based on the airflow rate exceeding a threshold; and generate a no inhalation error based on the airflow rate not exceeding the threshold for a predetermined period of time after the mouthpiece cover of the inhaler is moved to an open position or based on the airflow rate not exceeding the threshold until the mouthpiece cover is moved from the open position to a closed position;

wherein the communication circuit is configured to transmit the inhalation event or the no inhalation event, and an airflow rate of the inhalation to an external device; and a software application residing on the external device, wherein the software application is configured to receive the inhalation event and the airflow rate data via a wireless interface of the external device, generate a good inhalation event when the airflow rate is between a lower and upper threshold, and generate an excessive inhalation event when the airflow rate is above the upper threshold, wherein the excessive inhalation event is indicative of the obstruction of the air vent of the inhaler.

15. The system of claim 14, wherein the pressure sensor is further configured to measure a change in pressure within the inhaler resulting from an exhalation into the mouthpiece, and the controller is configured to generate an exhalation event based the pressure measurement data indicating a positive change in pressure, and wherein the communication circuit is configured to transmit the exhalation event to the external device;

wherein the software application is further configured to receive the exhalation event and display a notification of the exhalation event via a display device of the external device.

16. The system of claim 14, wherein the inhaler comprises a Quick Response (QR) code that comprises a communication passkey that is unique to the inhaler;

wherein the software application is further configured to receive the communication passkey via the QR code to enable wireless communication between the inhaler and the external device.

17. The system of claim 14, wherein the controller is further configured to start a measurement cycle in response to movement of the mouthpiece cover of the inhaler from the closed position to the open position, and generate the no inhalation error event when the airflow rate does not exceed the lower threshold during the measurement cycle, wherein the measurement cycle persists for the predetermined period of time or until the mouthpiece cover is moved from the open position to the closed position, whichever comes first;

wherein the communication circuit is configured to send the no inhalation event to the external device; and wherein the software application is configured to receive the no inhalation event and display an indication of the no inhalation event via a display device of the external device.

18. The system of claim 14, wherein the controller is configured to generate a mouthpiece cover opening event in response to movement of the mouthpiece cover of the inhaler from the closed position to the open position to make a dose of the medication available to the flow pathway and expose the mouthpiece; and wherein the software application is further configured to determine a number of doses of the medication remaining in the reservoir based on a number of mouthpiece cover opening events received from the controller of the inhaler.

19. The system of claim 18, wherein the software application is further configured to determine the number of doses of the medication remaining in the reservoir based further on a number of inhalation events received from the controller of the inhaler.

20. The system of claim 18, wherein the software application is further configured to identify a refill event based on the number of mouthpiece cover opening events received from the controller of the inhaler.

* * * * *